(12) United States Patent
Hilvo et al.

(10) Patent No.: US 10,184,932 B2
(45) Date of Patent: Jan. 22, 2019

(54) USE OF CERAMIDES AND LPLS IN DIAGNOSING CVD

(71) Applicant: ZORA BIOSCIENCES, OY, Espoo (FI)

(72) Inventors: Mika Hilvo, Helsinki (FI); Reini Hurme, Espoo (FI); Reijo Laaksonen, Lempaala (FI); Virve Vaeisaenen, Veikkola (FI)

(73) Assignee: Zora Biosciences OY, Espoo (FI)

( * ) Notice: Subject to any disclaimer, the term of this patent is extended or adjusted under 35 U.S.C. 154(b) by 13 days.

(21) Appl. No.: 15/371,661

(22) Filed: Dec. 7, 2016

(65) Prior Publication Data

US 2017/0160264 A1 Jun. 8, 2017

Related U.S. Application Data

(60) Provisional application No. 62/264,097, filed on Dec. 7, 2015.

(51) Int. Cl.
*G01N 33/49* (2006.01)
*G01N 33/92* (2006.01)

(52) U.S. Cl.
CPC .......... *G01N 33/492* (2013.01); *G01N 33/92* (2013.01); *G01N 2800/2871* (2013.01); *G01N 2800/324* (2013.01); *G01N 2800/52* (2013.01)

(58) Field of Classification Search
CPC ................ G01N 33/492; G01N 33/92; G01N 2800/2871; G01N 2800/324; G01N 2800/52
USPC ........................................................ 514/250
See application file for complete search history.

(56) References Cited

U.S. PATENT DOCUMENTS

| 8,321,154 | B2 | 11/2012 | Adourian et al. |
| 9,046,538 | B2 | 6/2015 | Laaksonen et al. |
| 2013/0216560 | A1 | 8/2013 | Laaksonen et al. |
| 2014/0295466 | A1 | 10/2014 | Laaksonen et al. |
| 2014/0295467 | A1 | 10/2014 | Laaksonen et al. |

FOREIGN PATENT DOCUMENTS

EP 2293077 B1 5/2014

OTHER PUBLICATIONS

Fernandez et al., "Plasma Lipid Compostion and Risk of Developing Cardiovascular Disease", PLOS ONE, Aug. 2013, vol. 8, Issue 8, e71846, 8 pages.
Goncalves et al., "Evidence Supporting a Key Role of Lp-PLA2-Generated Lysophosphatidylcholine in Human Atherosclerotic Plaque Inflammation", Arterioscler Thromb Vasc Biol., 2012, vol. 32, pp. 1505-1512 and 11 pages of Supplement Material.
Tarasov et al., "Molecular Lipids Identify Cardiovascular Risk and Are Efficiently Lowered by Simvastatin and PCSK9 Deficiency", J Clin Endocrinal Metab., Jan. 2014, vol. 99, No. 1, E45-52 (published online Nov. 15, 2013), 16 pages.

*Primary Examiner* — Kristin A Vajda

(57) ABSTRACT

The present invention inter alia provides a method, and use thereof, of predicting CV events such as AMI, ACS, stroke, and CV death by determining the concentration of at least one ceramide of Formula I or one lysophospholipid of Formula II and/or III and at least one lysophospholipid of Formula IV, V, VI, VII and/or VIII in a biological sample and comparing those concentrations to a control. Finding an increased concentration of the at least one Formula I ceramide or Formula II and/or III lysophospholipid and a decreased concentration of the at least one Formula IV, V, VI, VII and/or VIII lysophospholipid indicates that the subject has an increased risk of developing one or more CV events. The present disclosure also provides a method, and use thereof, of diagnosing subjects suffering acute ischemia. Also provided are kits and compositions comprising the same for use in predicting and/or diagnosing CV events.

3 Claims, 1 Drawing Sheet

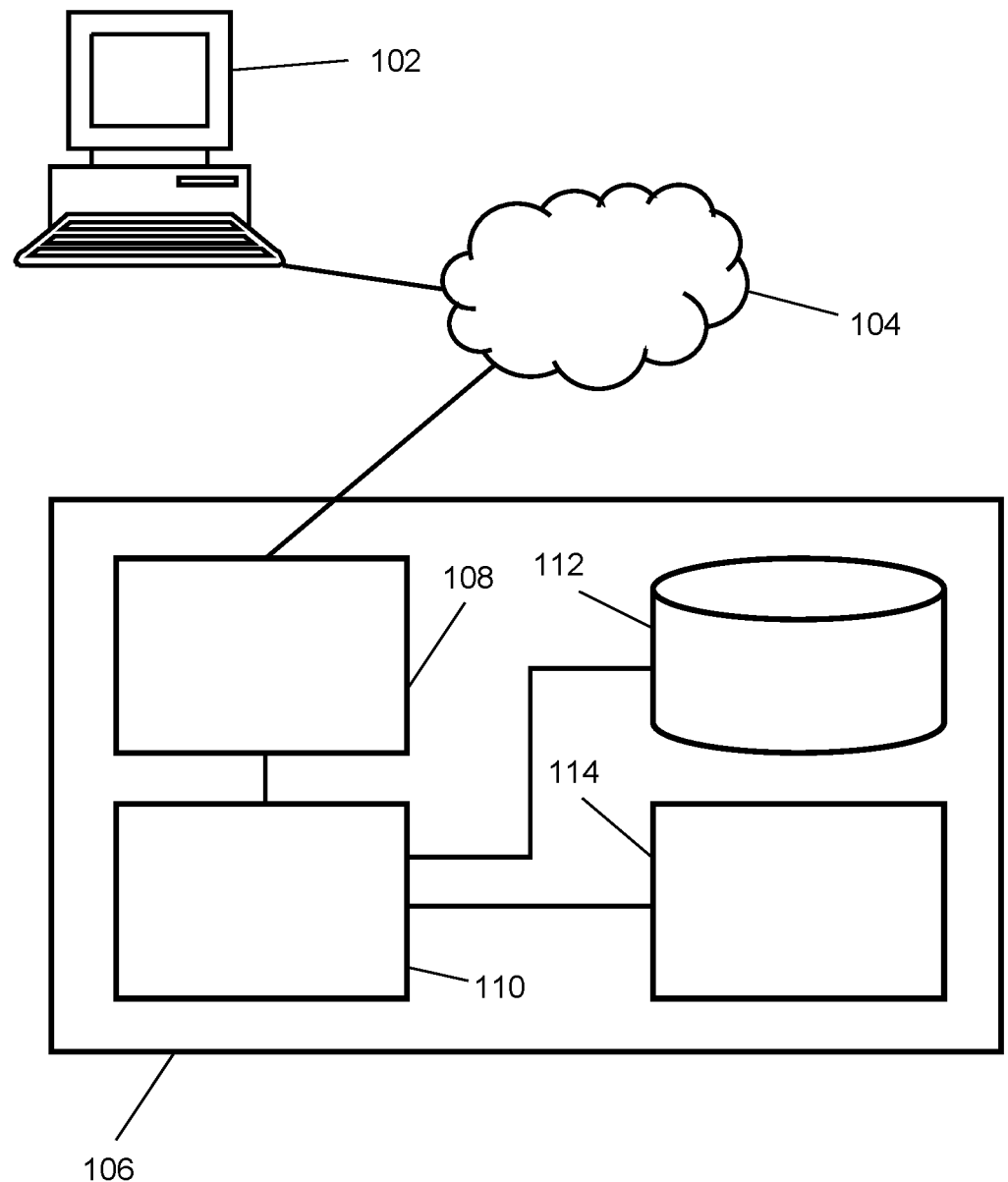

USE OF CERAMIDES AND LPLS IN DIAGNOSING CVD

CROSS REFERENCE TO RELATED APPLICATIONS

This application claims the benefit of priority of U.S. Provisional Application No. 62/264, 097, filed on 7 Dec. 2015, the entire disclosure of which is herein incorporated by reference.

FIELD

This application relates generally to lipid biomarkers and their use in identifying subjects having an increased risk for developing cardiovascular (CV) events, such as AMI (acute myocardial infarction), ACS (acute coronary syndrome), stroke, or CV death, and also their use in diagnosing subjects suffering from acute ischemia, as well as methods of treating subjects who have been identified according to such methods.

BACKGROUND

Current CV markers, LDL-C, LDL-P, and total cholesterol, are not able to identify coronary artery disease (CAD) patients or subjects that have an elevated risk for CV events, such as AMI, ACS, stroke and CV death, from patients having more stable disease.

The term myocardial infarction pathologically denotes the death of cardiac myocytes due to extended ischemia, which may be caused by an increase in perfusion demand or a decrease in blood flow. The event is called "acute" if it is sudden and serious. Diagnosis of AMI is determined by a high clinical suspicion from history and physical examination, in addition to changes in cardiac biomarkers (creatinine kinase MB [CK-MB], troponins, and myoglobin) and electrocardiogram (ECG) findings. Imaging techniques, such as two-dimensional echocardiography, are also useful in demonstrating myocardial dysfunction. Current CV markers, LDL-C, LDL-P, and total cholesterol, fail to predict the likelihood of the cardiovascular disease (CVD) event occurring.

Acute coronary syndrome (ACS) is a term used for any condition brought on by sudden, reduced blood flow to the heart. The first sign of acute coronary syndrome can be sudden stopping of the heart called cardiac arrest. Acute coronary syndrome is often diagnosed in an emergency room or hospital with the same cardiac biomarkers or electrocardiogram (ECG) as AMI, that provide evidence on damaged heart tissue or problems in the heart's electric activity.

A stroke is the loss of brain function due to a disturbance in the blood supply to the brain, depriving brain tissue of oxygen and food. Within minutes, brain cells begin to die. A stroke may be caused by a blocked artery (ischemic stroke) or a leaking or burst blood vessel (hemorrhagic stroke). Some people may experience a temporary disruption of blood flow through their brain (transient ischemic attack, or TIA). Strokes are usually diagnosed by brain imaging and carrying out physical tests.

Sudden cardiac death (SCD) is a sudden, unexpected death caused by loss of heart function, also named as sudden cardiac arrest (SCA). Sudden cardiac arrest is not a heart attack (myocardial infarction). Heart attacks occur when there is a blockage in one or more of the coronary arteries, preventing the heart from receiving enough oxygen-rich blood. In contrast, sudden cardiac arrest occurs when the electrical system to the heart malfunctions and suddenly becomes very irregular. The heart beats dangerously fast. Ventricular fibrillation may occur, and blood is not delivered to the body. In the first few minutes, the greatest concern is that blood flow to the brain will be reduced so drastically that a person will lose consciousness. Death follows unless emergency treatment is begun immediately. Sudden cardiac arrest happens without warning and is rarely diagnosed with medical tests as its happening. Instead, SCA often is diagnosed after it happens, by ruling out other causes of a person's sudden collapse.

AMI, ACS, stroke and sudden cardiac death are diagnosed in acute stage, but predictive markers are not available. The risk factors behind these events are for example, age, hypolipidemia, hypertension, smoking, diabetes, CAD or previous heart attack. Yet, no diagnostic test that could predict the events exists, and cardiovascular diseases are the leading cause of death worldwide. Furthermore, the costs to society that are associated with CVD are higher than for any other group of diseases. The same tests that are used for diagnosing CVD are utilized in predicting the events. Today the most innovative approach is to use LDL-C, LDL-P, HDL-C, Lp(a), Lp-PLA2 or CRP. However, none of the listed lipid based markers (LDL-C, LDL-P, Lp(a), Lp-PLA2) provide clinically useful predictive information allowing stratification to aid physicians. CRP has been promising in the research setting, however it has proven to be unspecific (CRP is an acute phase reactant that can react to many different stimuli leading to highly variable test results) and thus CRP values are difficult to interpret in the clinical use. There is an unmet need for a diagnostic test that could predict CV events, such as AMI (acute myocardial infarction), ACS (acute coronary syndrome), stroke and CV death.

Ischemia is a restriction in blood supply to tissues. When blood flow to the heart is reduced, the heart does not receive enough oxygen and nutrients, and the condition is called myocardial ischemia or cardiac ischemia. Myocardial ischemia can damage the heart muscle leading, e.g., to a heart attack. Therefore, an early detection of ischemia is crucial for survival of patients. There is an unmet need for diagnostic markers that could identify patients with early stage acute ischemia that can be either symptomatic or asymptomatic (silent ischemia).

The ceramide and lysophospholipid (LPL) based risk stratification offers improved performance compared to any other lipid based biomarker today.

Alterations in specific LPLs, i.e. lysophosphatidylcholines (LPCs), have been observed in primary prevention settings related to CAD (BG Medicine discloses EP2293077 and U.S. Pat. No. 8,321,154 as well as Fernandez et al., Plos one, 2013, 8(8):e71846). However, these studies have not provided information regarding the outcome of the patients, and therefore do not report those markers that could be used to identify CAD patients at high risk for future outcome events. Moreover, these studies did not investigate the association of ceramides related to CAD and did not investigate LPLs other than LPCs.

A large group of lipid molecules, including certain ceramides and LPCs, and ratios calculated from two lipid molecules have been identified for predicting CV outcomes in CAD patients who are undergoing statin treatment or who are not undergoing statin treatment or for identifying high-risk CAD patients or predicting whether a subject is at risk for developing CV events. However, there remains a desire for improved methods of predicting the risk of a patient developing a CV event, such as AMI, ACS, stroke, and CV death.

The current application recognizes value of both ceramides (Tarasov et al: J Clin Endocrinol Metab., 2014, 99(1):E45-52) and lysophospholipids (Goncalves et al., Arterioscler Thromb Vasc Biol. 2012 June; 32(6):1505-12

PMID:22499993) in development of CVD. It has earlier been reported that blood ceramide levels can be lowered by certain lipid lowering compounds including statin drugs (Tarasov et al., *J Clin Endocrinol Metab.*, 2014, 99(1):E45-52) and newly developed Lp-PLA2 inhibitors may potentially affect Lp-PLA2 mediated hydrolysis of low-density lipoprotein-oxidized phospholipids leading to generation of LPLs. Therefore, Cer/LPL-ratio can provide significant clinical improvement compared for instance to certain previously disclosed Cer/Cer-ratios as Cer/LPL-ratios can offer a better monitoring opportunity for the drug treatment effects; Cer can be affected by statin type of cholesterol lowering compounds, while LPL component may be controlled by drugs affecting for instance Lp-PLA2 activity.

This application provides new ceramide and LPL markers with superior AUC, sensitivity and specificity. This superior performance could not have been predicted from art known biomarkers.

SUMMARY

This application discloses a unique method for selecting combinations of ceramides and LPLs based on their structure and using them to predict CVD/CAD-associated (CV) events, including AMI, ACS, stroke, and CV death. These ceramide and LPL markers thus provide a means to identify and treat high-risk coronary artery disease patients. These sensitive and specific ceramide and LPL markers were specifically tested to display superior diagnostic and prognostic value compared to the current clinically-used markers predictive for CVD/CAD outcomes. Using combinations of ceramide and LPL biomarkers according to the newly established method will facilitate earlier intervention, less symptom development and suffering and decreased morbidity/mortality associated with CVD. Thus, the combination of ceramide and LPL markers described and claimed herein allow for individual tailoring of treatment, drug intervention and follow-up for patients being at risk to develop major CV events, such as AMI, ACS, stroke, and CV death.

According to this newly developed method, certain ceramides and certain LPLs have been classified into separate groups based on their structure and their association, when combined, (based on either an increased or decreased concentration) with an increased risk to develop CV events, such as AMI, ACS, stroke, and CV death. Thus, in certain embodiments, the instant methods involve determining the concentration of at least one ceramide of Formula I or one lysophosphatidylinositol (LPI) of Formula II and/or III and at least one LPC of Formula IV and/or V or at least one lysophosphatidic acid (LPA) of Formula VI and/or VII or at least one lysosphingomyelin (LSM) of Formula VIII in a biological sample obtained from a subject.

Ceramides of Formula (I) have the following structure:

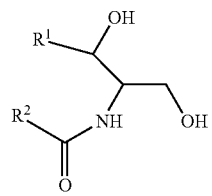

(I)

wherein $R^1$ is a mono-unsaturated alkyl chain having 13 carbon atoms or a saturated, mono-unsaturated or di-unsaturated alkyl chain having 15 carbon atoms, and wherein $R^1$ is a saturated alkyl chain having 15-21 carbon atoms, a mono-unsaturated alkyl chain having 21-23 carbon atoms or a di-unsaturated alkyl chain having 23 or 25 carbon atoms.

LPIs of Formulas (II and III respectively) have the following structures: (II) 1-acyl-2-lysoPI and (III) 2-acyl-1-lysoPI

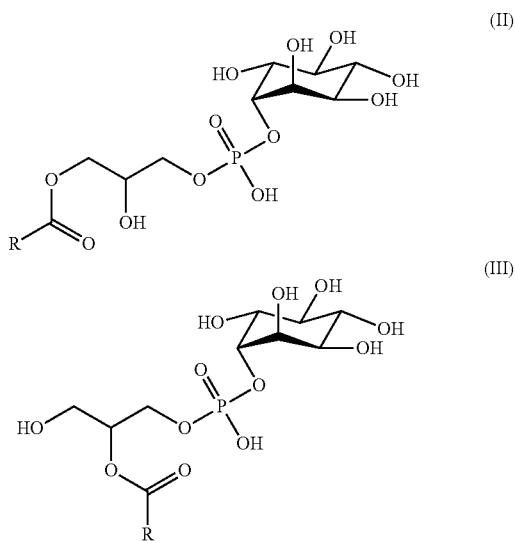

wherein R is a variable fatty acyl group of varying number of carbon atoms and number of double bonds, typically having 13-21 carbon atoms and 0-6 double bonds.

LPCs of Formulas (IV and V respectively) have the following structures: (IV) 1-acyl-2-lysoPC and (V) 2-acyl-1-lysoPC

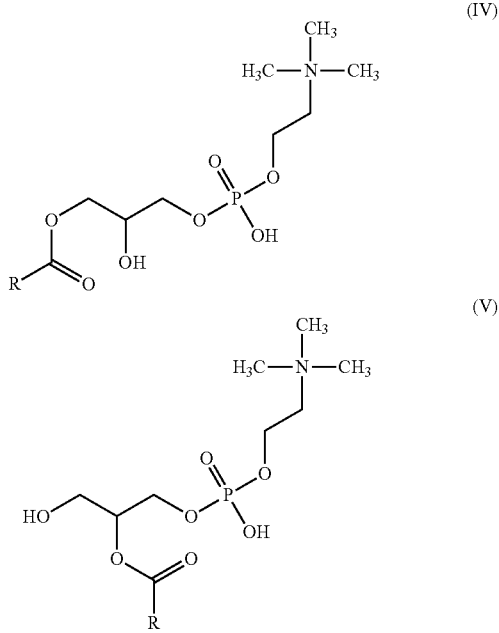

wherein R is a variable fatty acyl group of varying number of carbon atoms and number of double bonds, typically having 13-21 carbon atoms and 0-6 double bonds.

LPAs of Formulas (VI and VII respectively) have the following structures: (VI) 1-acyl-2-lysoPA and (VII) 2-acyl-1-lysoPA

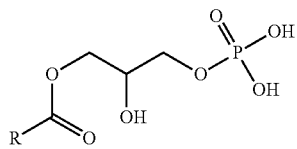

(VI)

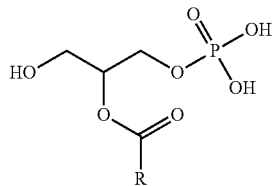

(VII)

wherein R is a variable fatty acyl group of varying number of carbon atoms and number of double bonds, typically having 13-21 carbon atoms and 0-6 double bonds.

LSMs of Formula VIII have the following structures:

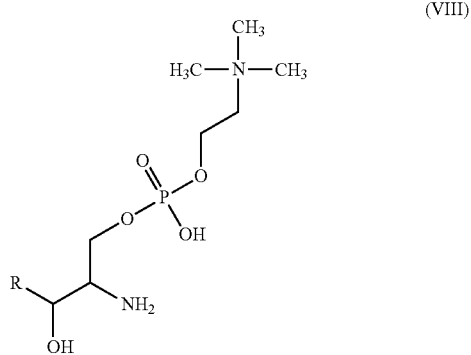

(VIII)

wherein R is a variable alkyl chain of varying number of carbon atoms and number of double bonds, typically having 13-17 carbon atoms and 0-2 double bonds.

In one embodiment, the method of determining whether a subject is at risk to develop one or more CV events includes the steps of: a) determining the concentration of at least one ceramide of Formula I or at least one LPL of Formula II and/or III in a biological sample obtained from the subject, b) determining the concentration of at least one LPL of Formula IV, V, VI, VII and/or VIII in the biological sample obtained from the subject, c) comparing the concentration of at least one ceramide of Formula I or at least one LPL of Formula II and/or III and the concentration of at least one LPL of Formula IV, V, VI, VII and/or VIII to a control sample; and d) determining that the subject has an increased risk of developing one or more CV events, if the sample contains an increased concentration of at least one ceramide of Formula I or at least one LPL of Formula II and/or III and a decreased concentration of at least one LPL of Formula IV, V, VI, VII and/or VIII, as compared to the control sample.

In one embodiment, the method of determining whether a subject is at risk to develop one or more CV events further includes after the determining step (d), (e) diagnosing the subject, such as a human subject, as having an increased risk of developing one or more CV events from the results in step (d); and (f) administering a treatment to the subject diagnosed in step (e).

In one aspect, the present disclosure is directed to a method of treating or preventing one or more CV events in a subject, such as a human subject, identified as being at risk to develop the one or more CV events, the method including: administering to the subject a treatment as described herein, wherein prior to administering the treatment, the subject has been identified as being at risk to develop the one or more CV events by the method of determining the risk as described herein.

In another aspect, the present disclosure is directed to a method of treating or preventing one or more CV events in a subject, such as a human subject, the method including: determining whether the subject is at risk to develop the one or more CV events according to the method of determining the risk as described herein, including administering to the subject a treatment, if the subject has been identified as being at risk to develop the one or more CV events.

Another aspect relates to a method for evaluating the effectiveness of a treatment of CVD and/or one or more of its events, such as AMI, ACS, stroke, and CV death, in a subject, the method including the steps of a) determining the concentration of at least one ceramide of Formula I or at least one LPL of Formula II and/or III in a biological sample obtained from the subject, b) determining the concentration of at least one LPL of Formula IV, V, VI, VII and/or VIII in the biological sample obtained from the subject, c) comparing the concentration of the at least one ceramide of Formula I or at least one LPL of Formula II and/or III and the concentration of the at least one LPL of Formula IV, V, VI, VII and/or VIII to a control sample; and d) determining that the treatment is effective if the sample contains an equal or decreased concentration of the at least one ceramide of Formula I or the at least one LPL of Formula II and/or III and an equal or increased concentration of the at least one LPL of Formula IV, V, VI, VII and/or VIII, as compared to the control sample.

In one embodiment, the method for evaluating the effectiveness of a treatment of atherosclerosis or CVD and/or one or more of its events in the subject, such as a human subject, further includes after step (d), (e) determining that the treatment is not effective in the subject from the results in step (d); and (f) escalating the treatment of the subject.

In certain embodiments, the escalation of the treatment regimen is as prescribed in relevant guidelines such that a subject will be moved to the next recommended tier based on an unfavorable change in concentration of the at least one ceramide of Formula I or at least one LPL of Formula II and/or III and the at least one LPL of Formula IV, V, VI, VII and/or VIII obtained in the determining step.

In one embodiment, the treatment regimen determined to be ineffective includes the administration of a lipid lowering drug as described herein. In certain embodiments, the relevant guidelines include increasing the dosage or the type of drug administered to the subject in comparison to the dosage or the type of drug administered before the determining step (d).

In one aspect, the present disclosure is directed to a method of treating or preventing CVD and/or one or more CV events in a subject, such as a human subject, undergoing treatment for CVD, the method including: administering to the subject a lipid lowering drug as described herein, wherein, prior to administering the lipid lowering drug, the subject has been identified as being ineffectively treated for CVD and/or the one or more CV events by the method for evaluating the effectiveness of a treatment as described herein.

In another aspect, the present disclosure is directed to a method of treating or preventing CVD and/or one or more CV events in a subject, such as a human subject, undergoing treatment for CVD, the method including: determining whether the subject is being ineffectively treated for CVD and/or the one or more CV events according to the method for evaluating the effectiveness of a treatment as described herein, and administering to the subject a lipid lowering drug, if the subject has been identified as being ineffectively treated for CVD and/or one or more CV events.

Yet another aspect relates to a method of choosing an appropriate treatment of CVD and/or one or more of its events, such as AMI, ACS, stroke, and CV death, in a subject, the method including the steps of a) determining the concentration of at least one ceramide of Formula I or at least one LPL of Formula II and/or III in a biological sample obtained from the subject, b) determining the concentration of at least one LPL of Formula IV, V, VI, VII and/or VIII in the biological sample obtained from the subject, c) comparing the concentration of the at least one ceramide of Formula I or at least one LPL of Formula II and/or III and the concentration of the at least one LPL of Formula IV, V, VI, VII and/or VIII to a control sample; and d) determining that the subject is in need of treatment or a change in, or supplementation of, an already administered treatment if the sample contains an increased concentration of the at least one ceramide of Formula I or at least one LPL of Formula II and/or III and a decreased concentration of the at least one LPL of Formula IV, V, VI, VII and/or VIII, as compared to the control sample.

In one embodiment, the method of choosing an appropriate treatment of CVD and/or one or more of its events, such as AMI, ACS, stroke, and CV death, in a subject further includes after the determining step (d), (e) determining that the subject is in need of treatment or a change in, or a supplementation of, an already administered treatment from the results in step (d); and (f) administering to the subject the treatment that the subject is determined to be in need of in step (e).

According to the present disclosure, a treatment may include, for example, administering a drug and/or providing therapeutic and/or behavioural modification and/or surgical operation to the subject. The drug may be, for example, a statin, another lipid lowering drug, and/or a modulator of lipid concentrations and/or parameters as described elsewhere in the present disclosure. Behavioural modification may include, for example, lifestyle counselling, including, but not limited to, instructions and/or encouragement regarding a healthy diet, physical activity/exercise and/or smoking cessation. The surgical operation may be, for example, a procedure to open blocked arteries or bypass surgery.

In one embodiment, the treatment, the effectiveness of which is to be evaluated or which is to be chosen as appropriate in accordance with the methods described and claimed herein, is a lipid modifying treatment (e.g., statin or other lipid lowering drug as described elsewhere in this application).

Yet another aspect relates to a method of detecting in a biological sample obtained from a subject the concentration of at least one ceramide and at least one LPL, wherein the method includes the steps of: (a) determining in a biological sample obtained from the subject the concentration of (i) at least one ceramide of Formula I or (ii) at least one LPI of Formula II and/or III; (b) determining in the biological sample from the subject the concentration of (i) at least one LPC of Formula IV and/or V, (ii) at least one LPA of Formula VI and/or VII or (iii) at least one LSM of Formula VIII; (c) optionally comparing the concentration of the at least one ceramide of Formula I or the at least one LPL of Formula II and/or III and the concentration of the at least one LPL of Formula IV, V, VI, VII and/or VIII to a control sample.

In one embodiment, the concentration of at least one of the following lipids of Formula I, II and/or III is detected: Cer(d18:1/16:0), Cer(d18:1/18:0), Cer(d18:1/24:1) and LPI 20:4 and wherein the concentrations of at least one of the following lipids of Formula IV, V and/or VIII is detected: LPC 14:0, LPC 18:0, LPC 16:0 and LysoSM(d18:1); and wherein the concentrations of the detected lipids are compared to a control sample.

In one embodiment, the determining in step (a) of the method of detection includes assaying the concentration of the at least one ceramide as described herein or the at least one LPI as described herein using mass spectrometry and wherein said determining in step (b) includes assaying the concentration of the at least one LPC and/or the at least one LPA and/or the at least one LSM using mass spectrometry.

In one embodiment, the method of detection further includes obtaining a biological sample, such as a blood sample or a urine sample as described herein, from the subject prior to step (a).

Yet another aspect relates to a method for determining whether a human subject is suffering from acute ischemia, wherein the method includes: (a) determining in a biological sample obtained from the human subject a concentration of (i) at least one ceramide of Formula I or (ii) at least one LPI of Formula II and/or III; (b) determining in the biological sample from the human subject a concentration of (i) at least one LPC of Formula IV and/or V, (ii) at least one LPA of Formula VI and/or VII or (iii) at least one LSM of Formula VIII; (c) comparing the concentration of the at least one ceramide of Formula I or the at least one LPL of Formula II and/or III and the concentration of the at least one LPL of Formula IV, V, VI, VII and/or VIII to a control sample; and (d) determining that the human subject is suffering from acute ischemia if the biological sample contains an increased concentration of the at least one ceramide of Formula I or the at least one LPL of Formula II and/or III and a decreased concentration of the at least one LPL of Formula IV, V, VI, VII and/or VIII, as compared to the control sample.

In one embodiment, the method of determining whether a subject is suffering from acute ischemia further includes after the determining step (d), (e) diagnosing the subject, such as a human subject, as suffering from acute ischemia from the results in step (d); and (f) administering a treatment to the subject diagnosed in step (e).

In one aspect, the present disclosure is directed to a method of treating acute ischemia in a subject, such as a human subject, identified as suffering from acute ischemia, the method including: administering to the subject a treatment as described herein, wherein prior to administering the treatment, the subject has been identified as suffering from acute ischemia by the method described herein.

In another aspect, the present disclosure is directed to a method of treating acute ischemia in a subject, such as a human subject, the method including: determining whether the subject is suffering acute ischemia according to the method described herein, including administering to the subject a treatment, if the subject has been identified as suffering from acute ischemia.

In one aspect, the present disclosure is directed to a method of treating or preventing CVD in a subject, such as a human subject, and/or one or more CV events, including:

administering to the subject a lipid lowering drug as described herein, wherein, prior to administering the lipid lowering drug, the subject has been identified as being in need of a change in, or supplementation of an already administered treatment for CVD and/or the one or more CV events by the method of choosing an appropriate treatment as described herein.

In another aspect, the present disclosure is directed to a method of treating or preventing CVD and/or one or more CV events in a subject, such as a human subject, the method including: determining whether the subject needs a change in, or supplementation of an already administered treatment according to the method of choosing an appropriate treatment as described herein, including administering to the subject a lipid lowering drug as described herein, if the subject has been identified as needing a change in, or supplementation of the already administered treatment.

Yet another aspect relates to a method of treating or preventing CVD and/or one or more of its events, such as AMI, ACS, stroke, and CV death, in a subject, the method including administering to the subject a therapeutically effective dose of a drug, wherein the drug is a statin; a lipid lowering drug selected from an HMG-CoA reductase inhibitor other than a statin, niacin (nicotinic acid), a cholesterol absorption inhibitor (e.g. ezetimibe), a cholesteryl ester transfer protein (CETP), a bile acid sequestrant, a fibrate, a phytosterol, an anti-inflammatory drug (e.g. methotrexate, IL-1 mAb, TNF-alpha mAb) and a PCSK9 inhibitor; or a modulator of lipid/lipid concentration ratios selected from a small molecule, an antibody, an antisense RNA, a small interfering RNA (siRNA), and a natural or modified lipid, and wherein before administering the drug the subject has been identified as suffering from or having an increased risk of developing a CVD event, such as AMI, ACS, stroke, and CV death based on an increased concentration of the at least one ceramide of Formula I or at least one LPL of Formula II and/or III and a decreased concentration of the at least one LPL of Formula IV, V, VI, VII and/or VIII, as compared to the control sample.

In some embodiments, the CVD treatment or prevention method further comprises identifying the subject as in need of the treatment or prevention, for example, by requesting a test, for example, from a commercial laboratory, which provides the results of an assay useful for determining the concentration of the at least one ceramide and the at least one LPL and administering to the subject a therapeutically effective dose of the drug, if the subject has an increased concentration of the at least one ceramide of Formula I or the at least one LPL of Formula II and/or III and a decreased concentration of the at least one LPL of Formula IV, V, VI, VII and/or VIII, as compared to the control sample.

The concentrations of ceramides and LPLs in the biological samples can be determined using any currently available technique or later developed technology. In certain embodiments, the concentrations of the ceramides and LPLs are determined using mass spectrometry. In certain embodiments, the mass spectrometry instrument is coupled to a direct sample infusion method or to a high performance separation method.

In some embodiments, the biological sample from the subject and the control sample is a urine sample or a blood sample, and more typically a blood plasma sample or a blood serum sample. In certain embodiments, the blood sample is a blood spot dried on a filter. It may also be a fraction of blood, blood plasma or blood serum, e.g., a lipoprotein fraction thereof. Thus, in certain embodiments, the methods comprise a further step of extracting the lipids from the biological sample before determining the concentrations of the ceramides and LPLs. Alternatively, both the sample from the subject and the control sample may be a tissue sample, e.g., artery tissue, such as carotid artery tissue, or artery plaque material, such as carotid artery plaque material.

In some embodiments, the methods described herein further includes a step of spiking the biological sample with at least one isotope-labelled ceramide of Formula I or at least one isotope-labelled LPL of Formula II and/or III and/or at least one isotope-labelled LPL of Formula IV, V, VI, VII and/or VIII. In some embodiments the isotope may be deuterium.

Yet another aspect is a composition or a kit for predicting CV events or for performing any of the methods disclosed herein. In certain embodiments, the composition or the kit includes at least one isotope (e.g., deuterium)-labelled ceramide of Formula I and/or at least one LPL of Formula II and/or III and/or at least one isotope (e.g., deuterium)-labelled LPL of Formula IV, V, VI, VII and/or VIII.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

FIG. 1 provides a schematic diagram of a system according to some embodiments of the invention. In particular, this FIGURE illustrates various hardware, software, and other resources that may be used in implementations of computer system 106 according to disclosed systems and methods.

DETAILED DESCRIPTION

Reference will now be made in detail to various exemplary embodiments, examples of which are illustrated in the accompanying drawings and discussed in the detailed description that follows. It is to be understood that the following detailed description is provided to give the reader a fuller understanding of certain embodiments, features, and details of aspects of the invention, and should not be interpreted as limiting the scope of the invention.

1. Abbreviations

Unless indicated otherwise, the abbreviations used in this application have the following meanings: LPL: lysophospholipid; LPC: lysophosphatidylcholine; LPI: lysophosphatidylinositol; LPA: lysophosphatidic acid; LysoSM (LSM): lysosphingomyelin; PC: phosphatidylcholine; PI: phosphatidylinositol; PA: phosphatidic acid; SM: sphingomyelin; CVD: cardiovascular disease; CV: cardiovascular; AMI: acute myocardial infarction; ACS: acute coronary syndrome; LDL-C: low density lipoprotein cholesterol; LDL-P: low density lipoprotein particle number; CAD: coronary artery disease; CK-MB: creatinine kinase MB; ECG: electrocardiogram; TIA: transient ischemic attack; SCD: sudden cardiac death; SCA: sudden cardiac arrest; HDL-C: high density lipoprotein cholesterol; Lp(a): lipoprotein a; Lp-PLA2: lipoprotein-associated phospholipase A2; CRP: C-reactive protein; HMG-CoA: 3-hydroxy-3-methylglutaryl-coentzyme; CETP: cholesteryl ester transfer protein; PCSK9: proprotein convertase subtilisin/kexin type 9; RNA: ribonucleic acid; siRNA: small interfering RNA; SB: sphingoid base; FA: fatty acid; HG: phosphorylcholine headgroup; OH: hydroxyl group; AUC: area under the receiver operating characteristic curve; R: real numbers; ApoA-I: Apolipoprotein A-I; ApoA-II: Apolipoprotein A-II; ApoB: Apolipoprotein B; ApoC-III: Apolipoprotein C-III; MS: mass spectrometry; HPLC: high performance liquid chromatography; UPLC: ultra performance liquid chromatography; UHPLC: ultra high pressure liquid chromatography; MRM: multiple reaction monitoring; MPIS: multiple precursor ion; NL: neutral loss scanning.

2. Definitions

In order that the present invention may be more readily understood, certain terms are first defined. Additional definitions are set forth throughout the detailed description.

The terms "subject," "host," "patient," and "individual" are used interchangeably herein to refer to any mammalian subject for whom diagnosis or therapy is desired, particularly humans. The subject may have previously suffered from a cardiovascular disease event such as angina pectoris, myocardial infarction or stroke. The CVD may or may not be a result of atherosclerosis. Or the subject may be a healthy individual with no previous signs of CVD.

Cardiovascular disease (CVD) is a general term of art used to classify numerous conditions that affect the heart, heart valves, blood, and vasculature of the body, including, but not limited to, CAD. In the present disclosure the terms CVD and CAD may be used interchangeably.

As used herein, cardiovascular (CV) events include, but are not limited to, endothelial dysfunction, coronary artery disease, angina pectoris, myocardial infarction, atherosclerosis, congestive heart failure, hypertension, cerebrovascular disease, stroke, transient ischemic attack, deep vein thrombosis, peripheral artery disease, cardiomyopathy, arrhythmias, aortic stenosis, aneurysm, acute coronary syndrome, ischemic heart disease, acute ischemia, myocardial ischemia, cardiac ischemia, ischemic cardiomyopathy, cerebrovascular ischemia, cerebral ischemia, ischemic stroke, silent ischemia, skeletal muscle ischemia (claudication) and CV death. Such events frequently involve atherosclerosis. In the present disclosure the terms CV event and CVD event may be used interchangeably.

As used herein, ischemia is a restriction in blood supply to tissues that prevents tissues from receiving enough oxygen and nutrients. Ischemia includes, but is not limited to, acute ischemia, myocardial ischemia, cardiac ischemia, cerebrovascular ischemia, cerebral ischemia, ischemic stroke, transient ischemic attack, silent ischemia and skeletal muscle ischemia (claudication). In the present disclosure the terms ischemia and ischaemia may be used interchangeably.

As used herein, the term "computer-implemented method" means a method which utilizes a machine or apparatus to achieve its objective.

As used herein, the term "processor" means a device which is capable of interpreting and executing instructions. Specifically, a processor employs logic circuitry to receive input data and provide the appropriate output data. Processors can communicate with each other via a network.

As used in this application, a ceramide or the like means a ceramide of Formula I:

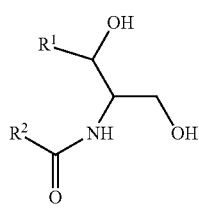

(I)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15-21 carbon atoms, a mono-unsaturated alkyl chain having 21-23 carbon atoms, or a di-unsaturated alkyl chain having 23 or 25 carbon atoms.

As used in this application, LPI or the like means an LPI of Formula II and III, respectively, having the following structures: (II) 1-acyl-2-lysoPI and (III) 2-acyl-1-lysoPI

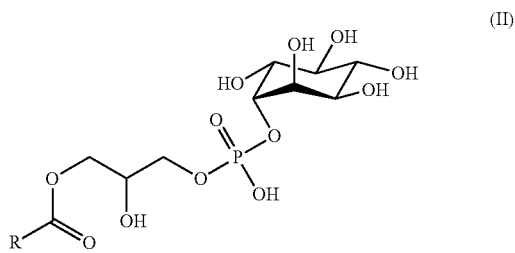

(II)

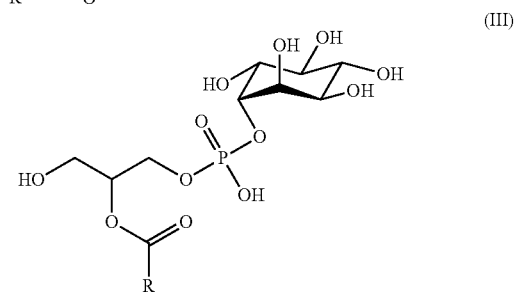

(III)

wherein R is a variable fatty acyl group of varying number of carbon atoms and number of double bonds, typically having 13-21 carbon atoms and 0-6 double bonds.

As used in this application, LPC or the like means an LPC of Formula IV and V, respectively, having the following structures: (IV) 1-acyl-2-lysoPC and (V) 2-acyl-1-lysoPC

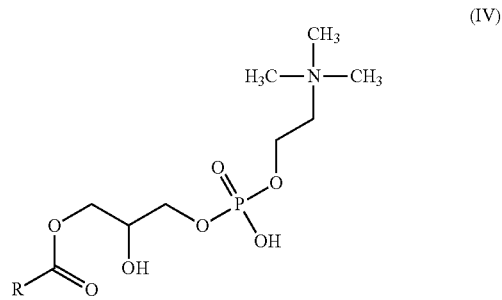

(IV)

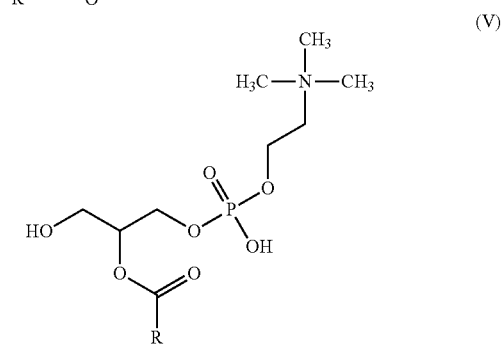

(V)

wherein R is a variable fatty acyl group of varying number of carbon atoms and number of double bonds, typically having 13-21 carbon atoms and 0-6 double bonds.

As used in this application, LPA or the like means an LPA of Formula VI and VII, respectively, having the following structures: (VI) 1-acyl-2-lysoPA and (VII) 2-acyl-1-lysoPA

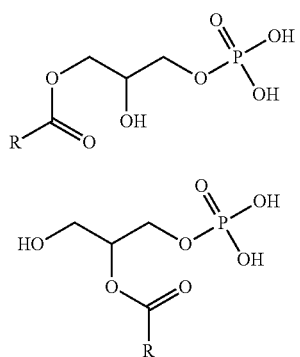

wherein R is a variable fatty acyl group of varying number of carbon atoms and number of double bonds, typically having 13-21 carbon atoms and 0-6 double bonds.

As used in this application, LSM or the like means an LSM of Formula VIII

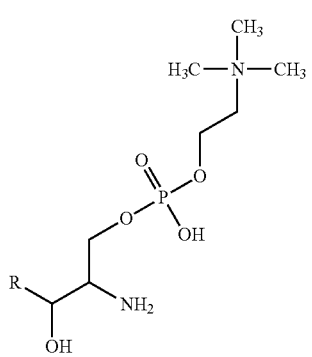

wherein R is a mono-unsaturated alkyl chain having 13 carbon atoms or a saturated, mono-unsaturated or di-unsaturated alkyl chain having 15 carbon atoms.

As used in this application, LPL (lysophospholipid) or the like encompasses an LPI, LPC, LPA and/or an LSM. LPL of Formula II and/or III refers to an LPI of Formula II and/or III, LPL of Formula IV and/or V refers to an LPC of Formula IV and/or V, LPL of Formula VI and/or VII refers to an LPA of Formula VI and/or VII and LPL of Formula VIII refers to an LSM of Formula VIII. In the present disclosure, the term LPL may be used interchangeably with terms LPI, LPC, LPA and/or LSM.

As used herein, a "lipid lowering drug" according to the disclosure is typically an HMG-CoA reductase inhibitor, niacin (nicotinic acid), a cholesterol absorption inhibitor, a cholesteryl ester transfer protein (CETP) inhibitor, a bile acid sequestrant, a fibrate, a phytosterol or a PCSK9 inhibitor.

As used herein, a "cholesterol absorption inhibitor" is typically, ezetimibe or SCH-48461; a cholesteryl ester transfer protein (CETP) inhibitor is typically evacetrapib, anacetrapib or dalcetrapib; a bile acid sequestrant is typically colesevelam, cholestyramine or colestipol; a fibrate is typically fenofibrate, gemfibrozil, clofibrate, or bezafibrate, an anti-inflammatory drug is typically methotrexane, IL-1 mAb or TNF-alpha mAb, and the PCSK9 inhibitor is selected from a PCSK9 specific antibody, a siRNA, and a peptidomimetic.

As used herein, a "statin" may be selected from, but not limited to, the group consisting of atorvastatin, fluvastatin, fluvastatin XL, lovastatin, pitavastatin, pravastatin, rosuvastatin and simvastatin.

The terms "of the disclosure", "in accordance with the disclosure", or "according to the disclosure" as used herein are intended to refer to all aspects and embodiments of the disclosure described and/or claimed herein.

As used herein, the term "comprising" is to be construed as encompassing both "including" and "consisting of", both meanings being specifically intended, and hence individually disclosed, embodiments in accordance with the present disclosure.

3. Ceramide Structure and Nomenclature

Ceramide molecules consists of sphingoid base (SB) and a fatty acid (FA) chain. The structure of one representative ceramide molecule is shown below.

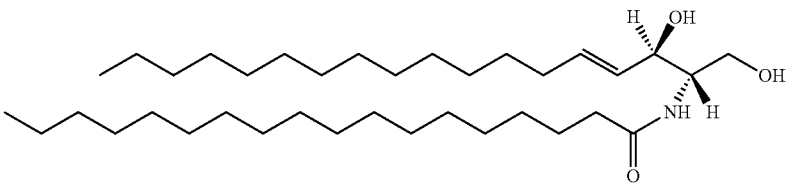 [SMILES: CCCCCCCCCCCCC/C=C/[C@@H](O)[C@H](CO)NC(=O)CCCCCCCCCCCCCCCCC]

This Cer(d18:1/18:0) lipid is a Formula I ceramide, where $R^1$ is a mono-unsaturated alkyl chain having 15 carbon atoms and $R^2$ is a saturated alkyl chain having 17 carbon atoms.

The nomenclature of ceramides is typically presented as a first pair of numbers corresponding to the SB and a second pair of numbers corresponding to the FA. For example, in the Cer(d18:1/18:0) molecule above, the first number pair (d18:1) refers to the SB and the second number pair (18:0) refers to the FA. In SB and FA nomenclature, the first number of each pair refers to the number of carbon atoms in the SB or FA chain, while the second number refers to the number of carbon-carbon double bonds of the SB or FA chain. Thus, in Cer(d18:1/18:0), the SB has 18 carbon atoms and one carbon-carbon double bond, while the FA has 18 carbon atoms and no carbon-carbon double bonds. FAs can be saturated or unsaturated depending on whether they have double bonds in their structure. For example, the FA 16:1 is an unsaturated FA with 16 carbon atoms and one carbon-carbon double bond, while the FA 18:0 is a saturated FA with 18 carbon atoms and no carbon-carbon double bonds.

By way of further example, the structure of Cer(d18:2/23:0) is as follows:

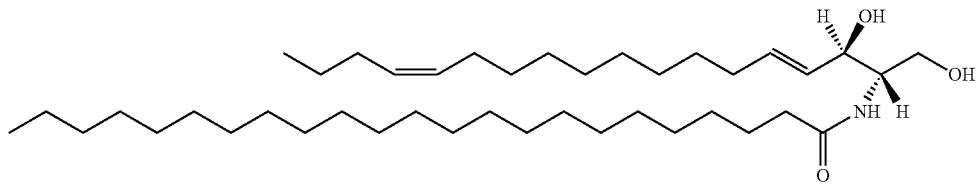 [SMILES: CCC/C=C\CCCCCCCC/C=C/[C@@H](O)[C@H](CO)NC(=O)CCCCCCCCCCCCCCCCCCCCCC]

This lipid is a Formula I ceramide, where $R^1$ is a di-unsaturated alkyl chain having 15 carbon atoms and $R^2$ is a saturated alkyl chain having 22 carbon atoms.

By way of further example, the structure of Cer(d16:1/22:1) is as follows:

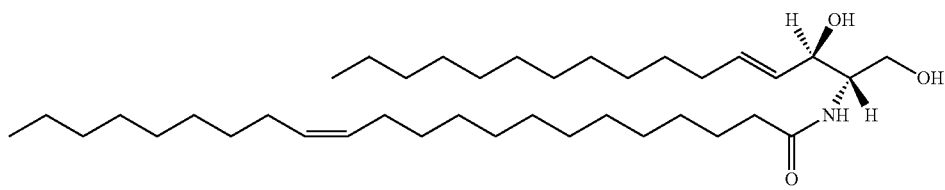 [SMILES: CCCCCCCC/C=C\CCCCCCCCCCCC(=O)N[C@@H](CO)[C@H](O)/C=C/CCCCCCCCCCC]

This lipid is a Formula I ceramide, where $R^1$ is a mono-unsaturated alkyl chain having 13 carbon atoms and $R^2$ is a mono-unsaturated alkyl chain having 21 carbon atoms.

In the de novo ceramide synthesis, the first double bond to the SB is formed in carbon 4, forming SBs d16:1 and d18:1. The second double bond of the SB is most commonly located in carbon 14, forming SB d18:2.

The double bond in the FA chain may be in various positions depending on the length of the FA chain and the number of carbon-carbon double bonds. In the 22:1 FA, the most common double bond position is in carbon 13. In the 23:1 FA, the most common double bond position is in carbon 14. In the 24:1 FA, the most common double bond position is in position 15. In the 24:2 and 26:2 FAs, the most common double bond positions are in carbons 5 and 9.

4. LPL Structure and Nomenclature

The 1-acyl-2-lysoPC and 2-acyl-1-lysoPC (LPC) molecules, corresponding to Formulas IV and V, respectively, have a phosphorylcholine headgroup (HG) attached to the sn-3 position of the glycerol backbone. 2-acyl-1-lysoPC molecules also have a hydroxyl group (OH) attached to the sn-1 position and a fatty acid (FA) chain attached to the sn-2 position of the glycerol backbone. For 1-acyl-2-lysoPC the hydroxyl and FA chains are inverted, with the hydroxyl group (OH) attached to the sn-2 position and the fatty acid (FA) chain attached to the sn-1 position of the glycerol backbone. The structures of representative LPC molecules are shown below.

1-Stearoyl-2-lysoPC (PC (18:0/0:0))

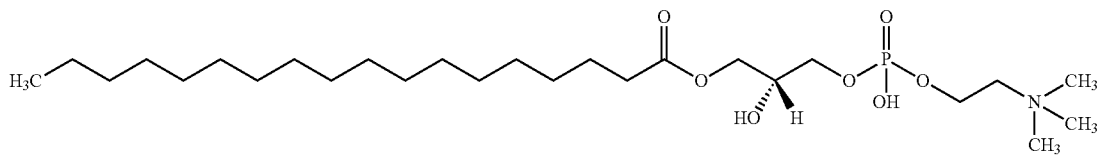

This 1-acyl-2-lysoPC molecule is PC(18:0/0:0), where R is a saturated acyl group having 17 carbon atoms, i.e. stearate (fatty acid 18:0) esterified to the sn-1 position of the glycerol backbone.

2-Stearoyl-1-lysoPC (PC(0:0/18:0))

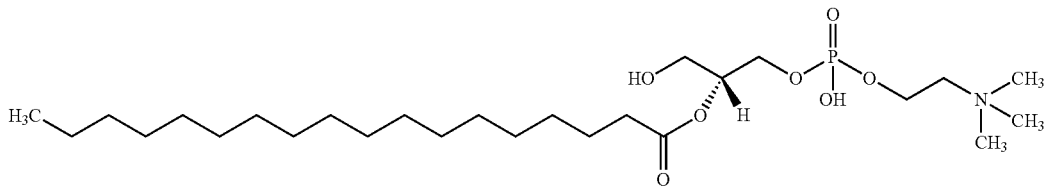

This 2-acyl-1-lysoPC molecule is PC(0:0/18:0), where R is a saturated acyl group having 17 carbon atoms, i.e. stearate (fatty acid 18:0) esterified to the sn-2 position of the glycerol backbone.

The nomenclature LPC refers to monoacylglycerophosphatidylcholine and typically includes both PC(18:0/0:0) and PC(0:0/18:0). The nomenclature LPC is typically presented with a number corresponding to the esterified FA. For example, in LPC 18:0, 18:0 refers to the FA attached either to the sn-1 or sn-2 position of the glycerol backbone. In FA nomenclature, the first number refers to the number of carbon atoms in the FA chain, while the second number refers to the number of carbon-carbon double bonds of the FA chain. Thus, in LPC 18:1, the FA has 18 carbon atoms and one carbon-carbon double bond. FAs can be saturated or unsaturated depending on whether they have double bonds in their structure. For example, the FA 16:1 is an unsaturated FA with 16 carbon atoms and one carbon-carbon double bond, while the FA 18:0 is a saturated FA with 18 carbon atoms and no carbon-carbon double bonds.

The 1-acyl-2-lysoPI and 2-acyl-1-lysoPI (LPI) molecules, corresponding to Formulas II and III, respectively, are otherwise identical with the PC(18:0/0:0) and PC(0:0/18:0) molecules, except that the phosphorylcholine headgroup attached to the sn-3 position is replaced by a phosphatidylinositol headgroup. The nomenclature LPI refers to monoacylglycerophosphoinositols and typically includes both 2-acyl-1-lysoPI and 1-acyl-2-lysoPI. The structures of representative LPI molecules are shown below.

1-Stearoyl-2-lysoPI 18:0 (PI(18:0/0:0))

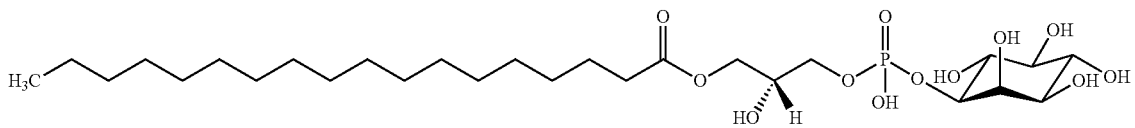

This 1-acyl-2-lysoPI molecule is PI(18:0/0:0), where R is a saturated acyl group having 17 carbon atoms, i.e. stearate (fatty acid 18:0) esterified to the sn-1 position of the glycerol backbone.

2-Stearoyl-1-lysoPI 18:0 (PI(0:0/18:0))

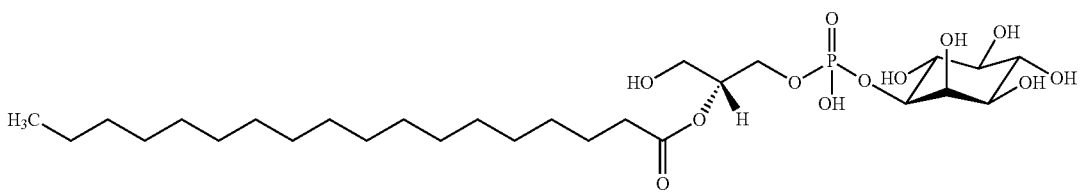

This 2-acyl-1-lysoPI molecule is PI(0:0/18:0), where R is a saturated acyl group having 17 carbon atoms, i.e. stearate (fatty acid 18:0) esterified to the sn-2 position of the glycerol backbone.

The 1-acyl-2-lysoPA and 2-acyl-1-lysoPA (LPA) molecules, corresponding to Formulas VI and VII, respectively, are otherwise identical with the PC(18:0/0:0) and PC(0:0/18:0) molecules, except that they do not contain the phosphorylcholine headgroup attached to the sn-3. The nomenclature LPA refers to monoacylglycerophosphates and typically includes both 2-acyl-1-lysoPA and 1-acyl-2-lysoPA. The structures of representative LPA molecules are shown below.

1-Stearoyl-2-lysoPA 18:0 (PA(18:0/0:0))

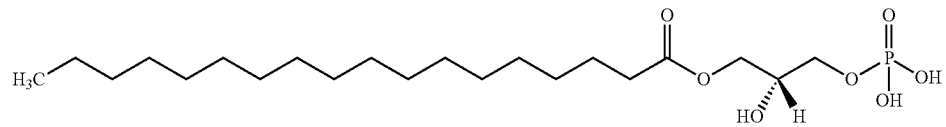 [SMILES: CCCCCCCCCCCCCCCCCC(=O)OC[C@@H](O)COP(=O)(O)O]

This 1-acyl-2-lysoPA molecule is PA(18:0/0:0), where R is a saturated acyl group having 17 carbon atoms, i.e. stearate (fatty acid 18:0) esterified to the sn-1 position of the glycerol backbone.

2-Stearoyl-1-lysoPA 18:0 (PA(0:0/18:0))

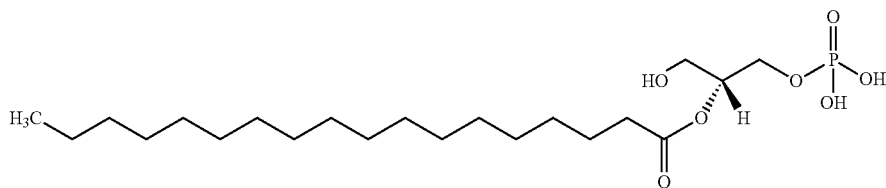 [SMILES: CCCCCCCCCCCCCCCCCC(=O)O[C@H](CO)COP(=O)(O)O]

This 2-acyl-1-lysoPA molecule is PA(0:0/18:0), where R is a saturated acyl group having 17 carbon atoms, i.e. stearate (fatty acid 18:0) esterified to the sn-2 position of the glycerol backbone.

The LSM molecules, corresponding to Formula VIII refers to lysosphingomyelins. The structure of a representative LSM molecule is shown below.

C17 sphingosine-1-phosphocholine SM(d17:1/0:0)

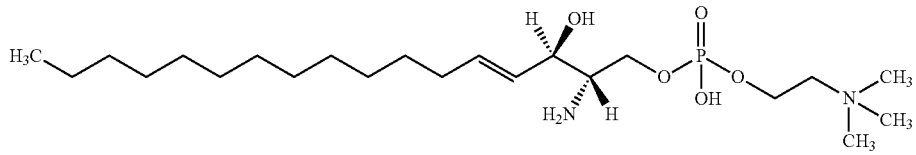

This LSM molecule is SM(d17:1/0:0), where R is a mono-unsaturated alkyl chain having 14 carbon atoms and a double bond at carbon position 4.

5. Diagnostic Methods

Disclosed herein are methods for predicting CV events including AMI, ACS, stroke and cardiovascular death, by measuring certain combinations of ceramides and LPLs in a biological sample. Ceramides have been implicated in the pathogenesis of CVD based on animal experiments, while the data in humans is largely lacking. We have recently shown the association of certain lipids, including certain distinct ceramide molecules, with CV mortality (U.S. Pat. Nos. 9,046,538, 9,201,080, 9,052,328, 9,052,327, and Tarasov et al., *J Clin Endocrinol Metab.*, 2014, 99(1):E45-52).

Disclosed herein are also methods for determining if a subject is suffering acute ischemia by measuring certain combinations of ceramides and LPLs in a biological sample.

For diagnostic use, a marker should have as high sensitivity and specificity as possible. Sensitivity measures the proportion of cases that are correctly classified as a case by the marker, and specificity measures the proportion of controls that are correctly classified as a control by the marker. For diagnostic use, it is important that a high enough percentage of subjects that are going to have a CV event in the future will be identified for targeted treatments at early stages. However, for limiting the treatment costs, in some embodiments markers with high specificity are preferred over markers with low specificity.

For example, a test with sensitivity of 0.7 would imply that among a population of 100 000 patients, that are going to face a CV event, 70 000 would be identified as having high risk for the event by the test. With a specificity of 0.2, among a population of 100 000 patients with stable CVD but with no forthcoming severe events, only 20 000 would be correctly identified of being low risk, while 80 000 would be falsely identified of being at high risk. The targeted treatment cost for 80 000 patients may be undesirable. In contrast, if an alternative test with a specificity value of 0.8 for the same event had been used, only 20 000 patients would be falsely identified having high risk for severe event. Compared to the low specificity test, this would save the treatment costs for 60 000 patients.

This application discloses methods for selecting a ceramide and an LPL lipid species to identify patients having increased risk for developing CV events with significantly improved AUC, sensitivity and specificity. This improved AUC, sensitivity and specificity is determined by the structure of the ceramides and the LPLs: an increased concentration of a ceramide species of Formula I or LPL of Formula II and/or III and a decreased concentration of an LPL species of Formula IV, V, VI, VII, VIII indicate an increased risk for developing CV events. In some embodiments, combinations of ceramide and LPL species by the disclosed methods are superior in predicting CV events compared to traditional risk markers or pairs of any lipid markers.

In a particular embodiment, a method is provided for determining whether a subject is at risk to develop one or more CV events, such as AMI, ACS, stroke, and CV death, wherein the method comprises (a) determining in a biological sample obtained from the subject the concentration of (i) at least one ceramide of Formula I or (ii) at least one LPI of Formula II and/or III;

(b) determining in the biological sample from the subject the concentration of (i) at least one LPC of Formula IV and/or V, (ii) at least one LPA of Formula VI and/or VII or (iii) at least one LSM of Formula VIII;

wherein each of the LPI, the LPC, the LPA and the LSM is a lysophospholipid (LPL);

(c) comparing the concentration of the at least one ceramide of Formula I or the at least one LPL of Formula II and/or III and the concentration of the at least one LPL of Formula IV, V, VI, VII and/or VIII to a control sample; and (d) determining that the subject has an increased risk of developing one or more CV events, if the biological sample contains an increased concentration of the at least one ceramide of Formula I or at least one LPL of Formula II and/or III and a decreased concentration of the at least one LPL of Formula IV, V, VI, VII and/or VIII, as compared to the control sample.

In one embodiment, the method of determining whether a subject is at risk to develop one or more CV events further comprises after the determining step (d), (e) diagnosing the subject, such as a human subject, as having an increased risk of developing one or more CV events from the results in step (d); and (f) administering a treatment to the human subject diagnosed in step (e).

In one aspect, the present disclosure is directed to a method of treating or preventing one or more CV events in a subject, such as a human subject, identified as being at risk to develop the one or more CV events, the method comprising: administering to the subject a treatment as described herein, wherein prior to administering the treatment, the subject has been identified as being at risk to develop the one or more CV events by the method of determining the risk as described herein.

In another aspect, the present disclosure is directed to a method of treating or preventing one or more CV events in a subject, such as a human subject, the method comprising: determining whether the subject is at risk to develop the one or more CV events according to the method of determining the risk as described herein, comprising administering to the subject a treatment, if the subject has been identified as being at risk to develop the one or more CV events.

Another aspect relates to a method for evaluating the effectiveness of a treatment of CVD and/or one or more of its events, such as AMI, ACS, stroke, and CV death, in a subject undergoing treatment for CVD, the method comprising the steps of (a) determining in a biological sample obtained from the subject the concentration of (i) at least one ceramide of Formula I or (ii) at least one LPI of Formula II and/or III;

(b) determining in the biological sample from the subject the concentration of
 (i) at least one LPC of Formula IV and/or V,
 (ii) at least one LPA of Formula VI and/or VII
 or (iii) at least one LSM of Formula VIII;
wherein each of the LPI, the LPC, the LPA and the LSM is a lysophospholipid (LPL);

(c) comparing the concentration of the at least one ceramide of Formula I or the at least one LPL of Formula II and/or III and the concentration of the at least one LPL of Formula IV, V, VI, VII and/or VIII to a control sample; and (d) determining that the treatment is effective if the sample contains an equal or decreased concentration of the at least one ceramide of Formula I or the at least one LPL of Formula II and/or III and an equal or increased concentration of the at least one LPL of Formula IV, V, VI, VII and/or VIII, as compared to the control sample.

In one embodiment, the method for evaluating the effectiveness of a treatment of atherosclerosis or CVD and/or one or more of its events in the subject, such as a human subject, further comprises after step (d), (e) determining that the treatment is not effective in the subject from the results in step (d); and (f) escalating the treatment of the subject.

In one aspect, the present disclosure is directed to a method of treating or preventing CVD and/or one or more CV events in a subject, such as a human subject, undergoing treatment for CVD, the method comprising: administering to the subject a lipid lowering drug as described herein, wherein, prior to administering the lipid lowering drug, the subject has been identified as being ineffectively treated for CVD and/or the one or more CV events by the method for evaluating the effectiveness of a treatment as described herein.

In another aspect, the present disclosure is directed to a method of treating or preventing CVD and/or one or more CV events in a subject, such as a human subject, undergoing treatment for CVD, the method comprising: determining whether the subject is being ineffectively treated for CVD and/or the one or more CV events according to the method for evaluating the effectiveness of a treatment as described herein, and administering to the subject a lipid lowering drug, if the subject has been identified as being ineffectively treated for CVD and/or the one or more CV events.

Yet another aspect relates to a method of choosing an appropriate treatment of CVD and/or one or more of its events, such as AMI, ACS, stroke, and CV death, in a subject, the method comprising:

(a) determining in a biological sample obtained from the subject the concentration of (i) at least one ceramide of Formula I or (ii) at least one LPI of Formula II and/or III;

(b) determining in the biological sample from the subject the concentration of
 (i) at least one LPC of Formula IV and/or V,
 (ii) at least one LPA of Formula VI and/or VII;
 or (iii) at least one LSM of Formula VIII;
wherein each of the LPI, the LPC, the LPA and the LSM is a lysophospholipid (LPL);

(c) comparing the concentration of the at least one ceramide of Formula I or the at least one LPL of Formula II and/or III and the concentration of the at least one LPL of Formula IV, V, VI, VII and/or VIII to a control sample; and (d) determining that the subject is in need of treatment or in need of adjusting the level of the treatment according to the appropriate guidelines on treating cardiovascular patients and the prescribed regimens and dosing therein if the sample contains an increased concentration of the at least one ceramide of Formula I or the at least one LPL of Formula II and/or III and an equal or decreased concentration of the at least one LPL of Formula IV, V, VI, VII and/or VIII, as compared to the control sample.

In one embodiment, the method of choosing an appropriate treatment of CVD and/or one or more of its events, such as AMI, ACS, stroke, and CV death, in a subject further comprises after the determining step (d), (e) determining that the subject, such as a human subject, is in need of treatment or a change in, or a supplementation of, an already administered treatment from the results in step (d); and (f) administering to the subject the treatment that the subject is determined to be in need of in step (e).

In one aspect, the present disclosure is directed to a method of treating or preventing CVD in a subject, such as a human subject, and/or one or more CV events, comprising: administering to the subject a lipid lowering drug as described herein, wherein, prior to administering the lipid lowering drug, the subject has been identified as being in need of a change in, or supplementation of an already administered treatment for CVD and/or the one or more CV events by the method of choosing an appropriate treatment as described herein.

In another aspect, the present disclosure is directed to a method of treating or preventing CVD and/or one or more CV events in a subject, such as a human subject, the method comprising: determining whether the subject needs a change in, or supplementation of an already administered treatment according to the method of choosing an appropriate treatment as described herein, comprising administering to the subject a lipid lowering drug as described herein, if the subject has been identified as needing a change in, or supplementation of the already administered treatment.

Yet another aspect relates to a method for determining whether a human subject is suffering from acute ischemia, the method comprising:
(a) determining in a biological sample obtained from the human subject a concentration of (i) at least one ceramide of Formula I or (ii) at least one LPI of Formula II and/or III;
(b) determining in the biological sample from the human subject a concentration of (i) at least one LPC of Formula IV and/or V, (ii) at least one LPA of Formula VI and/or VII or (iii) at least one LSM of Formula VIII, wherein each of the LPI, the LPC, the LPA and the LSM is a lysophospholipid (LPL);
(c) comparing the concentration of the at least one ceramide of Formula I or the at least one LPL of Formula II and/or III and the concentration of the at least one LPL of Formula IV, V, VI, VII and/or VIII to a control sample; and
(d) determining that the human subject is suffering from acute ischemia if the biological sample contains an increased concentration of the at least one ceramide of Formula I or the at least one LPL of Formula II and/or III and a decreased concentration of the at least one LPL of Formula IV, V, VI, VII and/or VIII, as compared to the control sample.

In one embodiment, the method of determining whether a subject is suffering from acute ischemia further comprises after the determining step (d), (e) diagnosing the subject, such as a human subject, as suffering from acute ischemia from the results in step (d); and (f) administering a treatment to the subject diagnosed in step (e).

In one aspect, the present disclosure is directed to a method of treating acute ischemia in a subject, such as a human subject, identified as suffering from acute ischemia, the method comprising: administering to the subject a treatment as described herein, wherein prior to administering the treatment, the subject has been identified as suffering from acute ischemia by the method described herein.

In another aspect, the present disclosure is directed to a method of treating acute ischemia in a subject, such as a human subject, the method comprising: determining whether the subject is suffering acute ischemia according to the method described herein, comprising administering to the subject a treatment, if the subject has been identified as suffering from acute ischemia.

In one embodiment of the aforementioned methods, the concentration of at least one of the following ceramides of Formula I is determined: Cer(d18:1/16:0), Cer(d18:1/18:0) and Cer(d18:1/24:1). In another embodiment, the concentration of the following LPI of Formula II and/or III is determined: LPI 20:4. Yet in another embodiment, the concentration of at least one of the following LPCs of Formula IV and/or V is determined: LPC 14:0, LPC 16:0 and LPC 18:0. Yet in another embodiment, the concentration of the following LSM of Formula VIII is determined: LysoSM(d18:1).

Yet in another embodiment, the concentration ratio of at least one of the following ceramides of Formula I: Cer(d18:1/16:0), Cer(d18:1/18:0) and Cer(d18:1/24:1) or the following LPI of Formula II and/or III: LPI 20:4 and at least one of the following LPCs of Formula II and/or III: LPC 14:0, LPC 16:0 and LPC 18:0 or the following LSM of Formula VIII is determined: LysoSM(d18:1).

In other embodiments, the concentration of the following ceramides of Formula I: Cer(d18:1/16:0), Cer(d18:1/18:0) and Cer(d18:1/24:1) and LPC 14:0 are determined. In other embodiments, the concentration of the following ceramides of Formula I: Cer(d18:1/16:0), Cer(d18:1/18:0) and Cer(d18:1/24:1) and LPC 16:0 are determined. In other embodiments, the concentration of the following ceramides of Formula I: Cer(d18:1/16:0), Cer(d18:1/18:0) and Cer(d18:1/24:1) and LPC 18:0 are determined. In other embodiments, the concentration of the following ceramides of Formula I: Cer(d18:1/16:0), Cer(d18:1/18:0) and Cer(d18:1/24:1) and LysoSM(d18:1) are determined. In another embodiment, the concentration of the following ceramides of Formula I: Cer(d18:1/16:0), Cer(d18:1/18:0) and Cer(d18:1/24:1) and LPC 14:0, LPC 16:0, LPC 18:0 and LysoSM(d18:1) are determined.

In another embodiment, the concentration of the following LPI of Formula II and/or III: LPI 20:4 and LPC 14:0 are determined. In other embodiments, the concentration of the following LPI of Formula II and/or III: LPI 20:4 and LPC 16:0 are determined. In other embodiments, the concentration of the following LPI of Formula II and/or III: LPI 20:4 and LPC 18:0 are determined. In other embodiments, the concentration of the following LPI of Formula II and/or III: LPI 20:4 and LysoSM(d18:1) are determined. In another embodiment, the concentration of the following LPI of Formula II and/or III: LPI 20:4 and LPC 14:0, LPC 16:0, LPC 18:0 and LysoSM(d18:1) are determined.

In yet other embodiments, at least one of the following ceramide/LPL concentration ratios is determined: Cer(d18:1/16:0)/LysoSM(d18:1), Cer(d18:1/16:0)/LPC:18:0, Cer(d18:1/16:0)/PC(18:0/0:0), Cer(d18:1/16:0)/PC(0:0/18:0), Cer(d18:1/18:0)/LPC 18:0 and Cer(d18: 1/24: 1)/LysoSM(d18: 1).

In yet other embodiments, at least one of the following LPI/LPL concentration ratios is determined: LPI 20:4/LPC 14:0, LPI 20:4/LPC 18:0, PI(20:4/0:0)/PC(14:0/0:0), PI(20:4/0:0)/PC(0:0/14:0), PI(20:4/0:0)/PC(18:0/0:0), PI(20:4/0:0)/PC(0:0/18:0) and LPI 20:4/LPC 16:0.

In one embodiment of the aforementioned methods, the concentrations of at least 2, at least 3, at least 4, at least 5, or at least 6 ceramides of Formula I or LPLs of Formula II and/or III and at least one LPL of Formula IV, V, VI, VII and/or VIII are determined. In another embodiment, the concentrations of at least one ceramide of Formula I or LPLs of Formula II and/or III and the concentration of at least 2, at least 3, at least 4, at least 5, or at least 6 LPLs of Formula IV, V, VI, VII and/or VIII are determined. In yet another embodiment, the concentrations of at least 2, at least 3, at least 4, at least 5, or at least 6 ceramides of Formula I or LPLs of Formula II and/or III are determined and the concentrations of at least 2, at least 3, at least 4, at least 5, or at least 6 LPLs of Formula IV, V, VI, VII and/or VIII are determined.

In certain embodiments of the aforementioned methods, the subject's risk of developing one or more CV events is determined according to the following equation: $Z = a \log (\text{ceramide (I) or LPL (II/III)}) + b \log (\text{LPL (IV-VIII)})$, wherein $a, b \in R$ and (ceramide) and (LPL) refer to the concentration of the ceramide and LPL, respectively. According to this embodiment the subject has an increased risk of developing one or more CV events, if the biological sample contains an increased Z value, as compared to the control sample. In another embodiment, the equation is used for determining that the treatment is effective if the sample contains an equal or decreased Z value, as compared to the control sample. In another embodiment, the Z value is calculated for determining that the subject is in need of treatment or in need of adjusting the level of the treatment according to the appropriate guidelines on treating cardiovascular patients and the prescribed regimens and dosing therein if the sample contains an increased Z value, as compared to the control sample.

In certain embodiments of the aforementioned methods, the methods further comprise a step of spiking the biological sample with at least one isotope-labelled ceramide of Formula I or at least one isotope-labelled LPL of Formula II and/or III and/or at least one isotope-labelled LPL of Formula IV, V, VI, VII and/or VIII. In some embodiments the isotope may be deuterium.

It may be useful and even advantageous for the methods and uses described herein to further comprise a step of determining the serum level of total cholesterol, low-density lipoprotein cholesterol (LDL-C), high-density lipoprotein cholesterol (HDL-C), Apolipoprotein A-I (ApoA-I), Apolipoprotein A-II (ApoA-II), Apolipoprotein B (ApoB) and/or Apolipoprotein C-III (ApoC-III) in a sample from said subject. Furthermore, according to one embodiment of the disclosed methods or uses, the subject is typically one that does not have elevated serum levels of one or more of total cholesterol, low-density lipoprotein cholesterol (LDL-C), Apolipoprotein C-III (ApoC-III) or Apolipoprotein B (ApoB), or a decreased serum level of HDL-cholesterol (HDL-C).

6. Detection Methods

Also disclosed herein are methods of detecting in a biological sample obtained from a subject the concentration of at least one ceramide and at least one LPL, wherein the method comprises:

(a) determining in a biological sample obtained from the subject the concentration of (i) at least one ceramide of Formula I or (ii) at least one LPI of Formula II and/or III;

(b) determining in the biological sample from the subject the concentration of (i) at least one LPC of Formula IV and/or V, (ii) at least one LPA of Formula VI and/or VII or (iii) at least one LSM of Formula VIII;

(c) optionally comparing the concentration of the at least one ceramide of Formula I or the at least one LPL of Formula II and/or III and the concentration of the at least one LPL of Formula IV, V, VI, VII and/or VIII to a control sample.

In one embodiment of the aforementioned methods, the concentration of at least one of the following ceramides of Formula I is determined: Cer(d18:1/16:0), Cer(d18:1/18:0) and Cer(d18:1/24:1). In another embodiment, the concentration of the following LPI of Formula II and/or III is determined: LPI 20:4. Yet in another embodiment, the concentration of at least one of the following LPCs of Formula IV and/or V is determined: LPC 14:0, LPC 16:0 and LPC 18:0. Yet in another embodiment, the concentration of the following LSM of Formula VIII is determined: LysoSM(d18:1).

Yet in another embodiment, the concentration ratio of at least one of the following ceramides of Formula I: Cer(d18:1/16:0), Cer(d18:1/18:0) and Cer(d18:1/24:1) or the following LPI of Formula II and/or III: LPI 20:4 and at least one of the following LPCs of Formula II and/or III: LPC 14:0, LPC 16:0 and LPC 18:0 or the following LSM of Formula VIII is determined: LysoSM(d18:1).

In other embodiments, the concentration of the following ceramides of Formula I: Cer(d18:1/16:0), Cer(d18:1/18:0) and Cer(d18:1/24:1) and LPC 14:0 are determined. In other embodiments, the concentration of the following ceramides of Formula I: Cer(d18:1/16:0), Cer(d18:1/18:0) and Cer(d18:1/24:1) and LPC 16:0 are determined. In other embodiments, the concentration of the following ceramides of Formula I: Cer(d18:1/16:0), Cer(d18:1/18:0) and Cer(d18:1/24:1) and LPC 18:0 are determined. In other embodiments, the concentration of the following ceramides of Formula I: Cer(d18:1/16:0), Cer(d18:1/18:0) and Cer(d18:1/24:1) and LysoSM(d18:1) are determined. In another embodiments, the concentration of the following ceramides of Formula I: Cer(d18:1/16:0), Cer(d18:1/18:0) and Cer(d18:1/24:1) and LPC 14:0, LPC 16:0, LPC 18:0 and LysoSM(d18:1) are determined.

In another embodiment, the concentration of the following LPI of Formula II and/or III: LPI 20:4 and LPC 14:0 are determined. In other embodiments, the concentration of the following LPI of Formula II and/or III: LPI 20:4 and LPC 16:0 are determined. In other embodiments, the concentration of the following LPI of Formula II and/or III: LPI 20:4 and LPC 18:0 are determined. In other embodiments, the concentration of the following LPI of Formula II and/or III: LPI 20:4 and LysoSM(d18:1) are determined. In another embodiments, the concentration of the following LPI of Formula II and/or III: LPI 20:4 and LPC 14:0, LPC 16:0, LPC 18:0 and LysoSM(d18:1) are determined.

In yet other embodiments, at least one of the following ceramide/LPL concentration ratios is determined: Cer(d18:1/16:0)/LysoSM(d18:1), Cer(d18:1/16:0)/LPC:18:0, Cer(d18:1/16:0)/PC(18:0/0:0), Cer(d18:1/16:0)/PC(0:0/18:0), Cer(d18:1/18:0)/LPC 18:0 and Cer(d18:1/24:1)/LysoSM(d18:1).

In yet other embodiments, at least one of the following LPI/LPL concentration ratios is determined: LPI 20:4/LPC 14:0, LPI 20:4/LPC 18:0, PI(20:4/0:0)/PC(14:0/0:0), PI(20:4/0:0)/PC(0:0/14:0), PI(20:4/0:0)/PC(18:0/0:0), PI(20:4/0:0)/PC(0:0/18:0) and LPI 20:4/LPC 16:0.

In one embodiment of the aforementioned methods, the concentrations of at least 2, at least 3, at least 4, at least 5, or at least 6 ceramides of Formula I or LPLs of Formula II and/or III and at least one LPL of Formula IV, V, VI, VII and/or VIII are determined. In another embodiment, the concentrations of at least one ceramide of Formula I or LPLs of Formula II and/or III and the concentration of at least 2, at least 3, at least 4, at least 5, or at least 6 LPLs of Formula IV, V, VI, VII and/or VIII are determined. In yet another embodiment, the concentrations of at least 2, at least 3, at least 4, at least 5, or at least 6 ceramides of Formula I or LPLs of Formula II and/or III are determined and the concentrations of at least 2, at least 3, at least 4, at least 5, or at least 6 LPLs of Formula IV, V, VI, VII and/or VIII are determined.

In one embodiment, the determining in step (a) of the aforementioned methods of detection includes assaying the concentration of the at least one ceramide as described herein or the at least one LPI as described herein using mass spectrometry and the determining in step (b) of the aforementioned methods of detection includes assaying the concentration of the at least one LPC and/or the at least one LPA and/or the at least one LSM using mass spectrometry.

In one embodiment, the method of detection further includes obtaining a biological sample, such as a blood sample or a urine sample as described herein, from the subject prior to step (a).

In one embodiment of the aforementioned methods, the biological sample and the control sample comprise at least one isotope (e.g., deuterium) labelled ceramide of Formula I and at least one isotope (e.g., deuterium) labelled LPL of Formula II, III, IV, V, VI, VII and/or VIII. In general, the isotope-labelled ceramide or LPL will be the same ceramide or LPL that is being detected in the biological sample. For example, if the concentration of the following ceramides of Formula I: Cer(d18:1/16:0), Cer(d18:1/18:0) and Cer(d18:1/24:1) and LPC 14:0, LPC 16:0, LPC 18:0 and LysoSM (d18:1) are determined, the biological sample and the control sample will comprise an isotope-labelled Cer(d18:1/16:0), an isotope-labelled Cer(d18:1/18:0), an isotope-labelled Cer(d18:1/24:1), an isotope-labelled LPC 14:0, an isotope-labelled LPC 16:0, an isotope-labelled LPC 18:0 and an isotope-labelled LysoSM(d18:1).

In some embodiments of the aforementioned methods, the biological sample and/or the control sample is obtained from a subject, such as a human subject, who has previously suffered from a cardiovascular disease event as described herein. The cardiovascular disease event may or may not be a result of atherosclerosis. In some embodiments, the biological sample and/or the control sample is obtained from a healthy individual with no previous signs of CVD and/or no risk of a CV event. In some embodiments, the biological sample and/or the control sample is obtained from an individual who is at risk of developing a CV event, such as a major CV event, e.g., AMI, ACS, stroke or CV death. In some embodiments, the biological sample and/or the control sample is obtained from a subject who is a CAD patient with or without a history of a major CV event. The biological sample and/or the control sample may also be obtained from a subject who is undergoing treatment with a lipid lowering drug, such as a statin, as described herein.

7. Measuring Ceramide and LPL Concentrations

In connection with all aspects and embodiments described and claimed herein, the determination of the ceramide or lysophospholipid concentration is typically performed using an assay. Collecting information on the concentration of a ceramide from the sample of a subject and, where appropriate, a corresponding control sample, can be performed with various chemical and high-resolution analytical techniques. Suitable analytical techniques include, but are not limited to, mass spectrometry and nuclear resonance spectroscopy. Any high-resolution technique capable of resolving individual LPLs and ceramides or LPL and ceramide classes and providing structural information of the same can be used to collect the information on the LPL and ceramide markers in question, e.g., LPL and ceramide profile from the biological sample. Collecting the information on the ceramide and LPL markers with mass spectrometry (MS) is one of the typical embodiments of the disclosed methods. The MS instrument can be coupled to a direct sample infusion method, such as a robotic nanoflow ion source device, or to a high performance separation method such as high performance liquid chromatography (HPLC) or ultra performance liquid chromatography (UPLC).

Other methods can be used or combined with MS and/or HPLC/UPLC to detect the ceramides and LPLs of interest, including, for example, nuclear magnetic resonance spectroscopy, liquid chromatography, thin-layer chromatography, gas-chromatography, fluorescence spectroscopy or dual polarisation interferometry, and/or an immunoassay such as an ELISA. According to an alternative or further embodiment a ceramide and/or an LPL in a sample can be detected and/or quantified using a binding moiety capable of specifically binding the ceramide and/or the LPL. The binding moiety can include, for example, a member of a ligand-receptor pair, i.e., a pair of molecules capable of having a specific binding interaction. The binding moiety can also include, for example, a member of a specific binding pair, such as antibody-antigen, enzyme-substrate, nucleic acid-based ligands, other protein ligands, or other specific binding pairs known in the art.

In a typical embodiment, the ceramide and LPL concentrations are measured using mass spectrometry (MS), wherein the MS instrument may be coupled to direct infusion methods or high performance separation methods such as HPLC or UPLC.

8. Sample Preparation

In accordance with the methods described and claimed herein, both the biological sample from the subject and the control sample can be a urine sample or a blood sample, more typically a blood plasma sample or a blood serum sample. The sample may also be a dried blood spot. It may also be a fraction of blood, blood plasma or blood serum, e.g., a lipid fraction extracted from the sample such as a lipoprotein fraction.

Urine and/or blood samples may be obtained according to routine clinical practice. The blood sample can be taken in connection with, for example, measuring the cholesterol levels in the patients. The collected blood sample can be prepared and serum or plasma can be separated with techniques well known to a person skilled in the art. Vena blood samples can be collected from patients using a needle and a BD Vacutainer® Plastic Tubes or Vacutainer® Plus Plastic Tubes (BD Vacutainer® SST™ Tubes contain spray-coated silica and a polymer gel for serum separation). Serum can be separated from the collected blood sample, for example, by centrifugation at 1300 RCF for 10 min at room temperature and stored in small plastic tubes at −80° C. Plasma can be separated, for example, by centrifugation at 2,500×g at 4° C. for 5 minutes. A dried blood spot is prepared by placing a spot of blood on filter paper and allowing it to air dry. Lipoprotein fractions may be separated for example by ultra centrifugation.

Alternatively, both the sample from the subject and the control sample may also be a tissue sample, e.g., artery tissue, such as carotid artery tissue, or artery plaque material, such as carotid artery plaque material.

9. Controls

The ceramide and LPL levels in a biological sample obtained from a subject may be compared to a control. The control may be a biological sample from a healthy individual. The control may also be a sample from CAD patient(s) with no history of major CVD events. It may also be a sample that represents a combination of samples from a generalized population of healthy individuals or a sample that represents a combination of samples from a CAD patient population with no history of major CVD events. The biological sample may be a urine sample, whole blood, blood serum or blood plasma, or lipoprotein fraction of blood. It may also be a tissue sample. However, in a typical embodiment, the biological sample is plasma, serum or lipoprotein (e.g., an LDL) fraction.

Alternatively, the control may be a set of data concerning a ceramide and LPL marker in accordance with the present invention, e.g., information on the concentration of ceramide(s) and LPL(s) in accordance with the present invention in a sample when taken from a healthy individual, or in a combination of samples when taken from a generalized population of healthy individuals, or from CAD patient(s) with no history of major CVD events, or from a CAD patient population with no history of major CVD events. The information, and thus the corresponding set of data, may have been previously determined, calculated or extrapolated, or may have yet to be determined, calculated or extrapolated, or may also be taken from the literature.

In the methods of evaluating the effectiveness of a treatment, the control sample may be from a healthy individual, as discussed above, in which case, finding that the biological sample from the subject contains concentrations of at least one ceramide of Formula I or LPL of Formula II and/or III and at least one LPL of Formula IV, V, VI, VII and/or VIII that are about the same as or equal to the control sample (not significantly different) indicates that the treatment was effective. Alternatively, the control sample can be obtained from a subject who is at risk to develop one or more CV events, such as AMI, ACS, stroke, or CV death. In certain embodiments, the subject from whom the control sample is obtained is the same individual being treated, in which case a concentration of at least one ceramide of Formula I or LPL of Formula II and/or III that is decreased relative to the control sample and a concentration of at least one LPL of Formula IV, V, VI, VII and/or VIII that is increased relative to the control sample, indicates that the treatment was effective.

10. Composition and Kits

Another aspect is a kit for predicting CV events or for performing any of the methods disclosed herein, wherein the kit comprises at least one isotope (e.g., deuterium) labelled ceramide of Formula I and at least one isotope (e.g., deuterium) labelled LPL of Formula II, III, IV, V, VI, VII and/or VIII, and optionally one or more reagents for performing the method. Also encompassed are compositions comprising at least one isotope (e.g., deuterium) labelled ceramide of Formula I and at least one isotope (e.g., deuterium) labelled LPL of Formula II, III, IV, V, VI, VII and/or VIII.

In one embodiment, the Formula I isotope-labeled ceramides include, for example, Cer(d18:1/16:0), Cer(d18:1/18:0) and Cer(d18:1/24:1). In another embodiment, the isotope-labeled LPLs of Formula II and/or III include, for example, LPI 20:4. Yet, in another embodiment, the isotope-labeled LPLs of Formula IV and/or V include, for example, LPC 14:0, LPC 16:0 and LPC 18:0. Yet, in another embodiment, the isotope-labeled LPLs of Formula VIII include, for example, LysoSM(d18:1).

In other embodiments, the isotope-labeled ceramides and isotope-labeled LPLs include, for example, isotope-labeled Cer(d18:1/16:0), Cer(d18:1/18:0) and Cer(d18:1/24:1) of Formula I and isotope-labeled LPC 14:0 of Formula IV and/or V. In other embodiments, the isotope-labeled ceramides and isotope-labeled LPLs include, for example, Cer(d18:1/16:0), Cer(d18:1/18:0) and Cer(d18:1/24:1) of Formula I and LPC 16:0 of Formula IV and/or V. In other embodiments, the isotope-labeled ceramides and isotope-labeled LPLs include, for example, Cer(d18:1/16:0), Cer(d18:1/18:0) and Cer(d18:1/24:1) of Formula I and LPC 18:0 of Formula IV and/or V. In other embodiments, the isotope-labeled ceramides and LPLs include, for example, Cer(d18:1/16:0), Cer(d18:1/18:0) and Cer(d18:1/24:1) of Formula I and LysoSM(d18:1) of Formula VIII. In another embodiment, the isotope-labeled ceramides and isotope-labeled LPLs include, for example, Cer(d18:1/16:0), Cer(d18:1/18:0) and Cer(d18:1/24:1) of Formula I and LPC 14:0, LPC 16:0, LPC 18:0 of Formula IV and/or V and LysoSM(d18:1) of Formula VIII.

Yet in another embodiment, the compositions and kits include at least one of the following isotope-labeled ceramides of Formula I: Cer(d18:1/16:0), Cer(d18:1/18:0) and Cer(d18:1/24:1) or the following isotope-labeled LPI of Formula II and/or III: LPI 20:4 and at least one of the following isotope-labeled LPCs of Formula II and/or III: LPC 14:0, LPC 16:0 and LPC 18:0 or the following isotope-labeled LSM of Formula VIII: LysoSM(d18:1).

In another embodiment, the kits or compositions include isotope-labeled LPLs of Formula II and/or III, such as LPI 20:4 and LPC 14:0. In other embodiments, the kits or compositions include isotope-labeled LPLs of Formula II and/or III, such as LPI 20:4 and LPC 16:0. In other embodiments, the kits or compositions include isotope-labeled LPLs of Formula II and/or III, such as LPI 20:4 and LPC 18:0. In other embodiments, the kits or compositions include isotope-labeled LPLs of Formula II and/or III, such as LPI 20:4 and LysoSM(d18:1). In another embodiment, the kits or compositions include isotope-labeled LPLs of Formula II and/or III, such as LPI 20:4 and LPC 14:0, LPC 16:0, LPC 18:0 and of Formula VII, such as LysoSM(d18: 1).

In yet other embodiments, the composition or kits include at least one of the following combinations of isotope-labeled ceramides and isotope-labeled LPLs: i) Cer(d18:1/16:0) and LysoSM(d18:1), ii) Cer(d18:1/16:0) and LPC:18:0, iii) Cer (d18:1/16:0) and PC(18:0/0:0), iv) Cer(d18:1/16:0) and PC(0:0/18:0), v) Cer(d18:1/18:0)/LPC 18:0 and vi) Cer(d18: 1/24:1) and LysoSM(d18:1).

In yet other embodiments, the composition or kits include at least one of the following combinations of isotope-labeled LPLs: i) LPI 20:4 and LPC 14:0, ii) LPI 20:4 and LPC 18:0, iii) PI(20:4/0:0) and PC(14:0/0:0), iv) PI(20:4/0:0) and PC(0:0/14:0), v) PI(20:4/0:0) and PC(18:0/0:0), vi) PI(20: 4/0:0) and PC(0:0/18:0) and vii) LPI 20:4 and LPC 16:0.

In other embodiments, the kit or composition comprises at least 2, at least 3, at least 4, at least 5, or at least 6 isotope (e.g., deuterium)-labelled ceramides of Formula I and/or at at least 3, at least 4, at least 5, at least 6, at least 7, at least 8, or at least 9 isotope (e.g., deuterium)-labelled LPLs of Formula II, III, IV, V, VI, VII and/or VIII.

All kits disclosed herein may be accompanied by instructions to use them for predicting a CV event, such as AMI, ACS, stroke, and CV death.

11. Computer-Implemented Diagnostic Methods

In accordance with all aspects and embodiments disclosed herein, the methods provided may be computer-implemented.

In one embodiment, any of the computer-implemented methods of the disclosure may further comprise the steps of (i) obtaining by at least one processor information reflecting the concentration of at least one ceramide of Formula I or LPL of Formula II and/or III and at least one LPL of Formula IV, V, VI, VII and/or VIII in the biological sample; and (ii) outputting in user readable format the concentration of at least one ceramide of Formula I or LPL of Formula II and/or III and at least one LPL of Formula IV, V, VI, VII and/or VIII in the biological sample.

In another embodiment, the computer-implemented methods may further comprise a step of determining by at least one processor a percentage difference between a control and the concentration of at least one ceramide of Formula I or LPL of Formula II and/or III and at least one LPL of Formula IV, V, VI, VII and/or VIII in the biological sample; and a step of outputting in user readable format the percentage difference obtained in the determining step (iii).

In yet another embodiment, the computer-implemented methods may further comprise a step of determining whether a subject is at risk to develop one or more CV events based on the percentage difference obtained in the outputting step.

In one embodiment of the computer-implemented methods, the at least one ceramide of Formula I comprises Cer(d18:1/16:0), Cer(d18:1/18:0) and/or Cer(d18:1/24:1) and/or the at least one LPL of Formula II and/or III comprises LPI 20:4 and the at least one LPL of Formula IV, V, VI, VII and/or VIII comprises LPC 14:0, LPC 16:0, LPC 18:0 and/or LysoSM(d18:1).

In embodiments as shown in FIG. 1, computer system 106 may include one or more processors 110 coupled to random access memory operating under control of or in conjunction with an operating system. The processor(s) 110 in embodiments may be included in one or more servers, clusters, or other computers or hardware resources, or may be implemented using cloud-based resources. The operating system may be, for example, a distribution of the Linux™ operating system, the Unix™ operating system, or other open-source or proprietary operating system or platform. Processor(s) 110 may communicate with data store 112, such as a database stored on a hard drive or drive array, to access or store program instructions other data.

Processor(s) 110 may further communicate via a network interface 108, which in turn may communicate via the one or more networks 104, such as the Internet or other public or private networks, such that a query or other request may be received from client 102, or other device or service. Additionally, processor(s) 110 may utilize network interface 108 to send information, instructions, workflows query partial workflows, or other data to a user via the one or more networks 104. Network interface 104 may include or be communicatively coupled to one or more servers. Client 102 may be, e.g., a personal computer coupled to the internet.

Processor(s) 110 may, in general, be programmed or configured to execute control logic and control operations to implement methods disclosed herein. Processors 110 may be further communicatively coupled (i.e., coupled by way of a communication channel) to co-processors 114. Co-processors 114 can be dedicated hardware and/or firmware components configured to execute the methods disclosed herein. Thus, the methods disclosed herein can be executed by processor 110 and/or co-processors 114.

Other configurations of computer system 106, associated network connections, and other hardware, software, and service resources are possible.

The following Examples further define and describe embodiments herein.

EXAMPLES

Example 1

Study patients. The Corogene study is a prospective cohort study where 5000 consecutive Finnish patients were assigned to diagnostic coronary angiogram in the region of Helsinki University Central Hospital. In this study, 436 CVD patients with significant stenosis in at least one coronary artery were analyzed. In this nested case-control study, one control subject was matched for each case. The cases were CVD patients that experienced CV events during an average follow-up of 2.5 years. The matching controls were CVD patients, who did not experience CV events during the follow-up. The matching criteria included: age, gender, body mass index, statin use, smoking and type 2 diabetes.

Analytical methods. For quantification, LPLs and ceramides were extracted using a modified Folch lipid extraction performed on a Hamilton Microlab Star robot, as described in Jung H R et al., "High throughput quantitative molecular lipidomics." *Biochim Biophys Acta.* 2011 November; 1811(11):925-34, which is hereby incorporated by reference in its entirety. Samples were spiked with known amounts of non-endogenous synthetic internal standards. After lipid extraction, samples were reconstituted in chloroform:methanol (1:2, v/v) and a synthetic external standard was post-extract spiked to the extracts. The extracts were stored at −20° C. prior to MS analysis.

Ceramides were analyzed on a hybrid triple quadrupole/linear ion trap mass spectrometer (5500 QTRAP) equipped with an ultra high pressure liquid chromatography (UHPLC) system (Eksigent ultraLC 100 system) using multiple reaction monitoring (MRM)-based method in negative ion mode based on the description by Sullards M C et al., "Structure-specific, quantitative methods for analysis of sphingolipids by liquid chromatography-tandem mass spectrometry: "inside-out" sphingolipidomics." *Methods Enzymol.* 2007; 432:83-115, which is herein incorporated by reference in its entirety.

LPLs were analyzed on a hybrid triple quadrupole/linear ion trap mass spectrometer (5500 QTRAP) equipped with a robotic nanoflow ion source NanoMate TriVersa by shotgun lipidomics using multiple precursor ion (MPIS) and neutral loss scanning (NL) based on the descriptions by Stahlman et al, "High-throughput shotgun lipidomics by quadrupole time-of-flight mass spectrometry." *Journal of chromatography. B, Analytical technologies in the biomedical and life sciences.* 2009; 877:2664-2672, which is herein incorporated by reference in its entirety.

Masses and counts of detected peaks by mass spectrometry were converted into a list of corresponding lipid names and concentrations. Calibration lines were generated to determine the dynamic quantification range for each lipid class monitored, e.g., the quantification limits. Internal standards were used for quantifying endogenous lipid species. Calibration lines were used to determine the quantification limits of the method.

Stringent cutoff was applied for separating background noise from actual lipid peaks. Each sample was controlled and only accepted when fulfilling the acceptance criteria. Masses and counts of detected peaks were converted into a list of corresponding lipid names. Lipids were normalized to their respective internal standard and sample volume to retrieve their concentrations.

Statistical methods. Area under the receiver operating characteristic curve (AUC) describes the overall predictive performance of the marker. Its values are between 0 and 1, with 0.5 corresponding to random, 50/50 (e.g., coin flipping), predictions of the outcome, and higher values indicating better prediction accuracy in terms of sensitivity and specificity.

Results. In the example study, the ceramide and LPL concentrations in CAD patients with CV events during a follow-up were compared to control subjects without events. AUC, sensitivity and specificity values were calculated for the lipid ratios. Table 1a shows significantly improved AUC, sensitivity and specificity values of specific ceramide and LPL ratios selected according to the method disclosed herein to identify patients having increased risk for developing CV events compared to pairs of other lipid markers. Table 1b shows selected significant ceramide to ceramide ratios and Table 1c presents the results in the study population of this disclosure for the significant ceramide to LPL ratios mentioned in U.S. Pat. Nos. 9,046,538 and/or 9,201,080, which are herein incorporated by reference in their entireties.

TABLE 1

Results from lipid to lipid ratios in the Corogene study cohort. Lipid ratio names, AUC, sensitivity and specificity are presented.

| Lipid ratio name | AUC | Sensitivity | Specificity |
|---|---|---|---|
| Table 1a. Selected significant lipid to lipid ratios. | | | |
| LPI 20:4/LPC 14:0 | 0.78 | 0.71 | 0.76 |
| Cer(d18:1/16:0)/Lyso SM(d18:1) | 0.77 | 0.72 | 0.73 |
| LPI 20:4/LPC 18:0 | 0.77 | 0.68 | 0.76 |

TABLE 1-continued

Results from lipid to lipid ratios in the Corogene study cohort. Lipid ratio names, AUC, sensitivity and specificity are presented.

| Lipid ratio name | AUC | Sensitivity | Specificity |
|---|---|---|---|
| Cer(d18:1/16:0)/LPC 18:0 | 0.77 | 0.71 | 0.72 |
| PI(20:4/0:0)/PC(14:0/0:0) | 0.77 | 0.74 | 0.75 |
| PI(20:4/0:0)/PC(0:0/14:0) | 0.77 | 0.71 | 0.75 |
| PI(20:4/0:0)/PC(18:0/0:0) | 0.77 | 0.69 | 0.70 |
| PI(20:4/0:0)/PC(0:0/18:0) | 0.77 | 0.73 | 0.74 |
| Cer(d18:1/16:0)/PC(18:0/0:0) | 0.77 | 0.72 | 0.72 |
| Cer(d18:1/16:0)/PC (0:0/18:0) | 0.77 | 0.68 | 0.73 |
| Cer(d18:1/18:0)/LPC 18:0 | 0.76 | 0.64 | 0.76 |
| LPI 20:4/LPC 16:0 | 0.75 | 0.71 | 0.73 |
| Cer(d18:1/24:1)/Lyso SM(d18:1) | 0.75 | 0.68 | 0.72 |
| Table 1b. Selected significant ceramide to ceramide ratios. | | | |
| Cer(d18:1/18:0)/Cer(d18:1/24:0) | 0.75 | 0.67 | 0.73 |
| Cer(d18:1/16:0)/Cer(d18:1/24:0) | 0.74 | 0.66 | 0.70 |
| Table 1c. Significant ceramide to LPC ratios mentioned in the prior art | | | |
| Cer(d18:1/18:0)/LPC 16:0 | 0.73 | 0.63 | 0.74 |
| Cer(d18:1/16:0)/LPC 18:2 | 0.73 | 0.72 | 0.64 |
| Cer(d18:1/24:1)/LPC 18:2 | 0.69 | 0.63 | 0.65 |

Results. In the example study, the ceramide and LPL concentrations in CAD patients with acute coronary syndrome, one form of ischemic heart disease, were compared to CAD patients without acute coronary syndrome. AUC, sensitivity and specificity values were calculated for the lipid ratios. Table 2 shows results for specific ceramide and LPL ratios selected according to the method disclosed herein to identify patients with ischemic heart disease.

TABLE 2

Results from lipid to lipid ratios in the Corogene study cohort for identifying patients with ischemic heart disease. Lipid ratio names, AUC, sensitivity and specificity are presented.

| Lipid ratio name | AUC | Sensitivity | Specificity |
|---|---|---|---|
| Table 2. Selected significant lipid to lipid ratios. | | | |
| Cer(d18:1/22:1)/LPA 16:0 | 0.78 | 0.71 | 0.74 |
| LPI 18:2/LPA 18:2 | 0.78 | 0.65 | 0.83 |
| LPI 18:2/PA (18:2/0:0) | 0.78 | 0.82 | 0.63 |
| PI (20:4/0:0)/PA (20:4/0:0) | 0.77 | 0.78 | 0.69 |
| PI (22:6/0:0)/LPA 18:1 | 0.77 | 0.66 | 0.81 |
| PI (22:6/0:0)/PA (18:1/0:0) | 0.77 | 0.64 | 0.84 |
| PI (22:6/0:0)/LPC 14:0 | 0.76 | 0.66 | 0.77 |
| PI (22:6/0:0)/PC (14:0/0:0) | 0.76 | 0.72 | 0.70 |
| PI (22:6/0:0)/PC (0:0/14:0) | 0.76 | 0.69 | 0.76 |
| Cer(d18:1/16:0)/LPA 16:0 | 0.75 | 0.67 | 0.69 |
| Cer(d18:1/16:0)/Lyso SM(d18:1) | 0.75 | 0.72 | 0.74 |
| Cer(d18:1/18:0)/LPA 16:0 | 0.75 | 0.72 | 0.73 |
| LPI 18:2/PA (0:0/18:2) | 0.75 | 0.7 | 0.74 |

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for determining whether a human subject is suffering from acute ischemia, wherein the method comprises:
(a) determining in a biological sample obtained from the human subject a concentration of (i) at least one ceramide of Formula I:

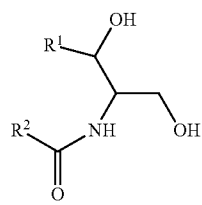

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15-21 carbon atoms, a monounsaturated alkyl chain having 21-23 carbon atoms, or a di-unsaturated alkyl chain having 23 or 25 carbon atoms, or (ii) at least one LPI of Formula II and/or III:

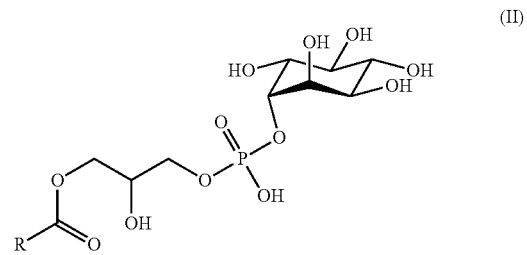

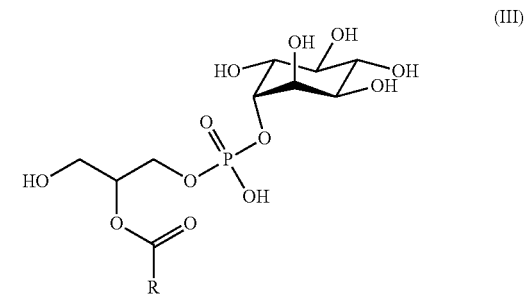

wherein R is a variable fatty acyl group of varying number of carbon atoms and number of double bonds;

(b) determining in the biological sample from the human subject a concentration of (i) at least one LPC of Formula IV and/or V:

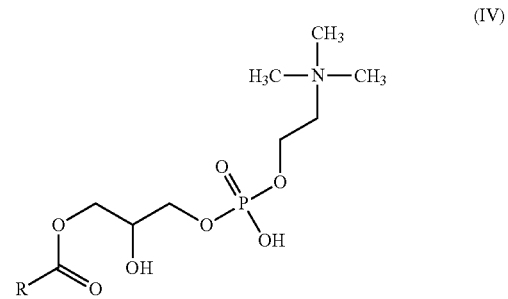

(V)

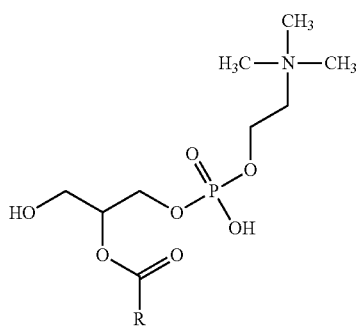

wherein R is a variable fatty acyl group of varying number of carbon atoms and number of double bonds, (ii) at least one LPA of Formula VI and/or VII:

(VI)

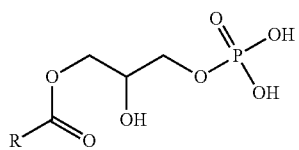

(VII)

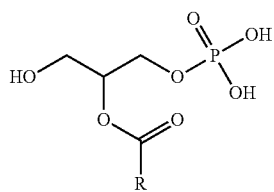

wherein R is a variable fatty acyl group of varying number of carbon atoms and number of double bonds, or (iii) at least one LSM of Formula VIII:

(VIII)

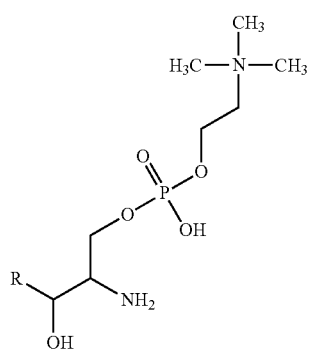

wherein R is a mono-unsaturated alkyl chain having 13 carbon atoms or a saturated, mono-unsaturated or di-unsaturated alkyl chain having 15 carbon atoms;

wherein each of the LPI, the LPC, the LPA and the LSM is a lysophospholipid (LPL), (c) comparing the concentration of the at least one ceramide of Formula I or the at least one LPL of Formula II and/or III and the concentration of the at least one LPL of Formula IV, V, VI, VII and/or VIII to a control sample; and (d) determining that the human subject is suffering from acute ischemia if the biological sample contains an increased concentration of the at least one ceramide of Formula I or the at least one LPL of Formula II and/or III and a decreased concentration of the at least one LPL of Formula IV, V, VI, VII and/or VIII, as compared to the control sample.

2. The method of claim 1, wherein the method further comprises:

(e) diagnosing the human subject as suffering from acute ischemia from the results in step (d);

(f) administering a treatment to the human subject diagnosed in step (e).

3. The method of claim 1, wherein R has 13-21 carbon atoms and 0-6 double bonds.

* * * * *